(12) United States Patent
Pradas et al.

(10) Patent No.: US 10,492,241 B2
(45) Date of Patent: Nov. 26, 2019

(54) PDCP UL SPLIT AND PRE-PROCESSING

(71) Applicant: TELEFONAKTIEBOLAGET LM ERICSSON (PUBL), Stockholm (SE)

(72) Inventors: Jose Luis Pradas, Stockholm (SE); Torsten Dudda, Aachen (DE); Henning Wiemann, Aachen (DE); Henrik Enbuske, Stockholm (SE)

(73) Assignee: Telefonaktiebolaget LM Ericsson (publ), Stockholm (SE)

( * ) Notice: Subject to any disclaimer, the term of this patent is extended or adjusted under 35 U.S.C. 154(b) by 0 days.

(21) Appl. No.: 16/227,430

(22) Filed: Dec. 20, 2018

(65) Prior Publication Data

US 2019/0132897 A1 May 2, 2019

Related U.S. Application Data

(63) Continuation of application No. PCT/IB2018/057464, filed on Sep. 26, 2018.
(Continued)

(51) Int. Cl.
*H04W 76/15* (2018.01)
*H04W 28/08* (2009.01)
(Continued)

(52) U.S. Cl.
CPC ........ *H04W 76/15* (2018.02); *G06F 9/45558* (2013.01); *H04W 24/08* (2013.01);
(Continued)

(58) Field of Classification Search
CPC ..... H04W 76/15; H04W 24/08; H04W 24/10; H04W 28/08; H04W 80/02; H04W 80/08; G06F 9/45558; G06F 2009/45595
See application file for complete search history.

(56) References Cited

U.S. PATENT DOCUMENTS

| 2014/0126399 | A1  | 5/2014  | Damnjanovic |
|---|---|---|---|
| 2018/0206213 | A1* | 7/2018  | Kim .................. H04L 69/22 |
| 2018/0352556 | A1* | 12/2018 | Loehr ................ H04L 1/1835 |

FOREIGN PATENT DOCUMENTS

| WO | 2016/159528 A1 | 10/2016 |
|---|---|---|
| WO | 2017/007147 A1 | 1/2017 |

OTHER PUBLICATIONS

Panasonic: "BSR Reporting Options for Dual Connectivity", 3GPP Draft; R2-140475 BSR Reporting in Dual Connectivity, 3rd Generation Partnership Project (3GPP), Mobile Competence Centre ; 650, Route Des Lucioles ; F-06921 Sophia-Antipolis Cedex ; France.
(Continued)

*Primary Examiner* — Thai Nguyen

(57) ABSTRACT

According to an aspect, a UE in an uplink split-bearer configuration is configured to transmit PDUs by a first RLC entity via a first uplink transmission path and/or by a second RLC entity via a second uplink transmission path. The UE determines a total amount of data volume from PDCP data volume and RLC data volume pending for initial transmission in the two RLC entities. The UE decides whether submission of PDCP data volume is allowed to either of the two RLC entities or to only the first RLC entity, based on whether the total amount of data volume meets or exceeds a first threshold. The UE also reports the PDCP data volume to both the first and second uplink transmission paths or only the first uplink transmission path, based on whether the total amount of data volume meets or exceeds a first threshold.

22 Claims, 13 Drawing Sheets

Related U.S. Application Data

(60) Provisional application No. 62/564,640, filed on Sep. 28, 2017.

(51) Int. Cl.
    *H04W 72/12*    (2009.01)
    *G06F 9/455*     (2018.01)
    *H04W 24/08*    (2009.01)
    *H04W 24/10*    (2009.01)
    *H04W 80/02*    (2009.01)
    *H04W 80/08*    (2009.01)

(52) U.S. Cl.
    CPC .......... *H04W 24/10* (2013.01); *H04W 28/08* (2013.01); *H04W 28/085* (2013.01); *H04W 72/1284* (2013.01); *G06F 2009/45595* (2013.01); *H04W 80/02* (2013.01); *H04W 80/08* (2013.01)

(56) References Cited

OTHER PUBLICATIONS

Samsung: "Data to be considered for BSR in uplink split bearer", 3GPP Draft; R2-152263 Data to be Considered, 3rd Generation Partnership Project (3GPP), Mobile Competence Centre ; 650, Route Des Lucioles; F-06921 Sophia-Antipolis Cedex; France.

\* cited by examiner

PDCP UL SPLIT AND PRE-PROCESSING

RELATED APPLICATIONS

This application is a Continuation of International Patent Application PCT/IB2018/057464, filed Sep. 26, 2018, which claims the benefit of U.S. Provisional Application No. 62/564,640, filed Sep. 28, 2017 and entitled "PDCP SPLIT AND PRE-PROCESSING," the disclosures of which are all hereby incorporated by reference.

TECHNICAL FIELD

The present invention is related to wireless communication networks, and particularly related to uplink split-bearer configurations for UEs that transmit packet data units, PDUs, by a first Radio Link Control, RLC, entity via a first uplink transmission path and/or by a second RLC entity via a second uplink transmission path.

BACKGROUND

In 3GPP Long Term Evolution (LTE), a user equipment (UE) can be configured with dual connectivity (DC), where the UE is connected to two separate eNBs, associated via separate Medium Access Control (MAC) entities/cell groups. In the uplink (UL) split bearer configuration of DC, the UE maintains one Packet Data Convergence Protocol (PDCP) entity that routes the data via two separate Radio Link Control (RLC) entities, via the two cell groups to the two eNBs.

When a UE is configured with DC and UL split bearer, the UE is configured with two UL transmission paths associated with two separate RLC entities. Transmission on these transmission paths is triggered by reception of an UL transmission grant from the eNB for the respective path. In LTE, the PDCP entity delivers PDCP Protocol Data Units (PDUs) to the RLC entity for transmission when a transmission opportunity is indicated by lower layers, or when requested by lower layers for this path (i.e., upon grant reception). A PDCP PDU is then delivered to the RLC entity and the RLC entity builds an RLC PDU. This implies that PDCP stores the PDCP PDUs and does not deliver them to lower layers until requested by them. The RLC state variables are only updated when PDCP delivers a PDCP PDU to the RLC entity.

When the PDCP data volume is above a configured split threshold, the UE reports that data as available for transmission to both eNBs, otherwise the report is only towards a configured prioritized eNB (i.e., for a single prioritized path). In both cases, the network may then issue grants independently to each of the paths. This behavior allows the network to control the load that each of the paths carries. This is currently specified as a procedure to report uplink data available at PDCP to a Master Cell Group (MCG) and Secondary Cell Group (SCG) when a pre-configured threshold amount of data is exceeded.

In 3GPP New Radio (NR), the PDCP entity can deliver a PDCP PDU to the RLC entity at any point in time and the RLC entity can also build an RLC PDU at any point in time, even before a transmission opportunity is indicated by lower layers. This means that the UE pre-selects the path in which the PDCP PDUs are placed regardless of whether the UE has a grant or not in that path. In contrast to LTE, the UE in NR reports part of the available data to the first path, part of the other data to the second path, and may still report part of the data that was not yet delivered to one of the two RLC entities to both paths.

SUMMARY

The existing solution for NR, as indicated above, greatly reduces the ability of the network to control the load on each of the paths. Compared to LTE, in NR, the RLC entity will buffer data (RLC PDUs) and will wait for a grant to be received. The RLC state variable TX_NEXT (which indicates the next Sequence Number to be set for the upcoming RLC SDU) is also updated any time a new RLC PDU is created and queued.

Creating RLC PDUs without having a transmission opportunity creates a number of issues. For example, the network is not able to control the traffic load in each of the paths because the UE pre-determines in which path the UE stores data and in which path grants are requested. Also, if RLC PDUs are stored for a long period of time due to the fact that no grants are received, very few grants or small grant sizes are received. If there are many RLC PDU retransmissions in at least one of the RLC entities in which RLC PDUs are stored, undesirable events may occur. The PDCP discard timer may expire, leading to data loss. The T-reordering timer in the PDCP receiver side may expire, leading to the discard of the data that was not received. Another issue is that data cannot be discarded (i.e., current LTE procedures for RLC SDU discard are obsolete). Unwanted jitter may also be introduced when the UE does not split the data to be transmitted according to the uplink grant ratio.

Another consideration involved with the pre-processing of PDUs by the RLC entities involves the buffer data volume that is to be compared to the PDCP uplink split bearer threshold. According to some embodiments, when PDCP PDUs are moved to RLC for the purpose of pre-processing, and the data is not transmitted yet, the pre-processed data at the RLC entity or entities should be considered as part of the data volume calculation for comparison with the uplink split bearer threshold. The threshold determines the amount of data buffered for transmission on the prioritized UL path, and thus should consider all data on both RLC and PDCP that is not yet transmitted.

For any buffer status reporting (BSR) or reporting of data volume, if the data volume falls below the split threshold, data is indicated only to the configured UL path. If the data volume is higher than the threshold, data is indicated to both UL paths.

According to some embodiments, a method by a UE configured to transmit PDUs by a first RLC entity via a first uplink transmission path and/or by a second RLC entity via a second uplink transmission path includes determining a total amount of data volume buffered for PDU transmission, where the total amount of data volume includes PDCP data volume and RLC data volume pending for initial transmission in the two RLC entities. The method also includes reporting the PDCP data volume to at least the first uplink transmission path, based on whether the total amount of data volume meets or exceeds a first threshold. The reporting includes, in response to determining that the total amount of data volume meets or exceeds the first threshold, indicating the PDCP data volume to both the first uplink transmission path and the second uplink transmission path, and, in response to determining that the total amount of data volume does not meet the first threshold, indicating the PDCP data volume to only the first uplink transmission path.

The first uplink transmission path may be configured as a prioritized uplink transmission path and the second uplink transmission path may be configured as an unprioritized uplink transmission path. The first RLC entity may belong to a Master Cell Group (MCG), and the second RLC entity may belong to a Secondary Cell Group (SCG).

While the (PDCP) data volume for BSR operation is the same as in LTE, for effective pre-processing implementation, the actual submission to lower procedure may need to be slightly different than in LTE. That is, when data volume is below the split threshold, it must be transmitted via the configured UL (while in LTE it was possible via either UL). In some embodiments, in response to determining that the total amount of data does not meet a first threshold, the method includes submitting the data volume only to the first RLC entity.

According to certain embodiments, when the data volume is below the PDCP split threshold, UE is not expected to have data available for transmission on the unprioritized UL path.

According to some embodiments, a method by a UE configured to transmit PDUs by a first RLC entity via a first uplink transmission path and/or by a second RLC entity via a second uplink transmission path includes determining a total amount of data volume buffered for PDU transmission, where the total amount of data volume includes PDCP data volume and RLC data volume pending for initial transmission in the two associated RLC entities. The method also includes deciding whether submission of the PDCP data volume is allowed to either of the two RLC entities or to only the first RLC entity, based on whether the total amount of data volume meets or exceeds a first threshold. The deciding includes, in response to determining that the total amount of data volume meets or exceeds the first threshold, deciding that the PDCP data volume is allowed to be submitted to either of the two RLC entities, and, in response to determining that the total amount of data volume does not meet the first threshold, deciding that the PDCP data volume is allowed to be submitted to only the first RLC entity.

The method may further include submitting the PDCP data volume according to the decision. The method may include, in response to deciding that the PDCP data volume is allowed to be submitted to either of the two RLC entities, submitting the PDCP data volume to whichever of the two RLC entities requested the PDCP data volume.

According to some embodiments, a UE is configured to transmit PDUs by a first RLC entity via a first uplink transmission path and/or by a second RLC entity via a second uplink transmission path. The UE includes transceiver circuitry configured to send and receive radio signals and processing circuitry operatively associated with the transceiver circuitry. The processing circuitry is configured to determine a total amount of data volume buffered for PDU transmission, where the total amount of data volume includes PDCP data volume and RLC data volume pending for initial transmission in the two RLC entities. The processing circuitry is also configured to report the PDCP data volume to at least the first uplink transmission path, based on whether the total amount of data volume meets or exceeds a first threshold. The reporting includes, in response to determining that the total amount of data volume meets or exceeds the first threshold, indicating the PDCP data volume to both the first uplink transmission path and the second uplink transmission path, and, in response to determining that the total amount of data volume does not meet the first threshold, indicating the PDCP data volume to only the first uplink transmission path.

According to some embodiments, a UE is configured to transmit PDUs by a first RLC entity via a first uplink transmission path and/or by a second RLC entity via a second uplink transmission path. The UE includes transceiver circuitry configured to send and receive radio signals and processing circuitry operatively associated with the transceiver circuitry. The processing circuitry is configured to determine a total amount of data volume buffered for PDU transmission, where the total amount of data volume comprises PDCP data volume and RLC data volume pending for initial transmission in the two associated RLC entities. The processing circuitry is also configured to decide whether submission of the PDCP data volume is allowed to either of the two RLC entities or to only the first RLC entity, based on whether the total amount of data volume meets or exceeds a first threshold. The deciding includes, in response to determining that the total amount of data volume meets or exceeds the first threshold, deciding that the PDCP data volume is allowed to be submitted to either of the two RLC entities, and, in response to determining that the total amount of data volume does not meet the first threshold, deciding that the PDCP data volume is allowed to be submitted to only the first RLC entity.

Embodiments described herein provide solutions to these or other challenges. According to one embodiment, a UE is configured to: 1) determine when an RLC PDU will be delivered too late (causing data losses); 2) re-route the data to a second path when the RLC PDU cannot be delivered on time in the first path; and 3) remove the RLC PDUs from the first path.

According to some embodiments, a UE is configured with a maximum pre-processing limit. This configuration may be indicated in RRC signaling from the gNB. The maximum pre-processing limit limits, in terms of time, pre-processing to close a transmission gap that may be created when, for example, PDU n+1 is transmitted while PDU n is not transmitted. The UE may not exceed the pre-processing limit and thus the UE may discard a pre-processed PDU for transmission via one path (cell group) and/or retransmit a pre-processed PDU via another path (another cell group).

The various embodiments described herein address one or more of the issues with uplink split-bearer transmission of PDUs. Certain embodiments may provide one or more technical advantages. For instance, certain embodiments may avoid packet loss that might occur when reordering delays that are too high are introduced. Unwanted jitter may also be avoided. According to certain embodiments, high throughputs may be enabled for UL resource aggregation with UL split configuration. All of these benefits lead to higher end user performance. Certain embodiments may provide all, some, or none of these specific advantages, and other advantages may be readily apparent.

Additional embodiments may include the method implemented by apparatus, wireless devices, computer readable medium, computer program products and functional implementations.

Of course, the present invention is not limited to the above features and advantages. Indeed, those skilled in the art will recognize additional features and advantages upon reading the following detailed description, and upon viewing the accompanying drawings.

DETAILED DESCRIPTION

Some of the embodiments contemplated herein will now be described more fully with reference to the accompanying drawings. Other embodiments, however, are contained within the scope of the subject matter disclosed herein, the disclosed subject matter should not be construed as limited to only the embodiments set forth herein; rather, these embodiments are provided by way of example to convey the scope of the subject matter to those skilled in the art.

Embodiments of the present invention improve UE operations in an uplink split bearer configuration. To improve the accuracy of transmission decisions, according to some embodiments, any PDCP PDUs that are moved to RLC for the purpose of pre-processing and are pending for initial transmission in RLC entities are considered with the PDCP data volume when the data volume is being compared to the PDCP uplink split bearer threshold. The uplink split bearer threshold determines the amount of data buffered for transmission on the prioritized uplink transmission path, and thus all data on both RLC and PDCP that is not yet transmitted should be considered.

Buffer status reporting (BSR) or other PDCP data reporting then involves the total amount of data volume that considers both the PDCP data volume and the data volume that is being pre-processed or buffered in the RLC layer before an uplink grant is received and before the data is transmitted. If the total data volume is below the uplink split bearer threshold, PDCP data volume is indicated only to the configured uplink transmission path. If the PDCP data volume is higher than the threshold, PDCP data volume is indicated to both uplink transmission paths.

Figure 1:
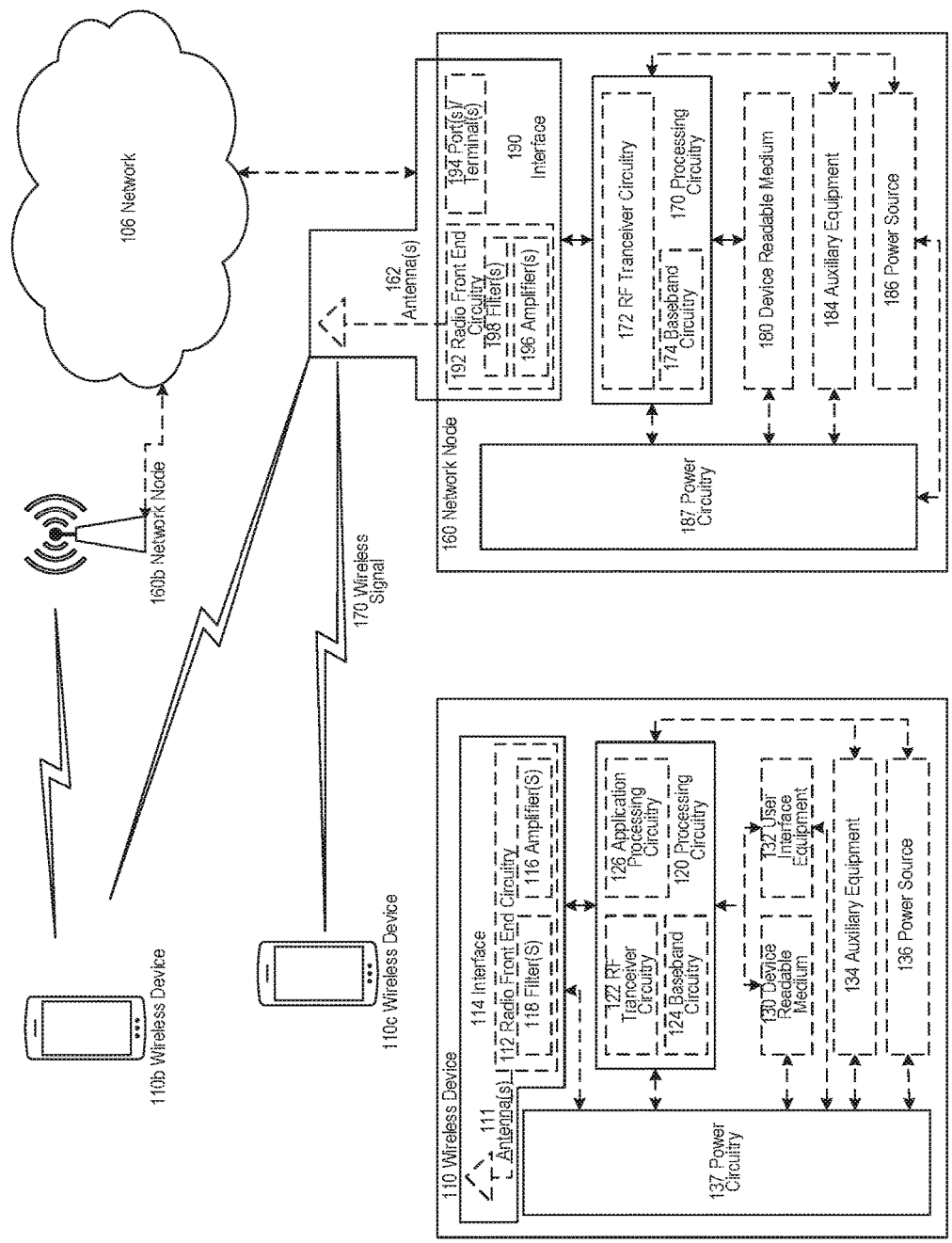
FIG. 1 illustrates a wireless communication network, according to some embodiments.

Although the subject matter described herein may be implemented in any appropriate type of system using any suitable components, the embodiments disclosed herein are described in relation to a wireless network, such as the example wireless network illustrated in FIG. 1. For simplicity, the wireless network of FIG. 1 only depicts network 106, network nodes 160 and 160*b*, and wireless devices (WDs) 110, 110*b*, and 110*c*. In practice, a wireless network may further include any additional elements suitable to support communication between wireless devices or between a wireless device and another communication device, such as a landline telephone, a service provider, or any other network node or end device. Of the illustrated components, network node 160 and WD 110 are depicted with additional detail. The wireless network may provide communication and other types of services to one or more wireless devices to facilitate the wireless devices' access to and/or use of the services provided by, or via, the wireless network.

The wireless network may comprise and/or interface with any type of communication, telecommunication, data, cellular, and/or radio network or other similar type of system. In some embodiments, the wireless network may be configured to operate according to specific standards or other types of predefined rules or procedures. Thus, particular embodiments of the wireless network may implement communication standards, such as Global System for Mobile Communications (GSM), Universal Mobile Telecommunications System (UMTS), Long Term Evolution (LTE), and/or other suitable 2G, 3G, 4G, or 5G (NR) standards; wireless local area network (WLAN) standards, such as the IEEE 802.11 standards; and/or any other appropriate wireless communication standard, such as the Worldwide Interoperability for Microwave Access (WiMax), Bluetooth, Z-Wave and/or ZigBee standards.

Network 106 may comprise one or more backhaul networks, core networks, IP networks, public switched telephone networks (PSTNs), packet data networks, optical networks, wide-area networks (WANs), local area networks (LANs), wireless local area networks (WLANs), wired networks, wireless networks, metropolitan area networks, and other networks to enable communication between devices.

Network node 160 and WD 110 comprise various components described in more detail below. These components work together in order to provide network node and/or wireless device functionality, such as providing wireless connections in a wireless network. In different embodiments, the wireless network may comprise any number of wired or wireless networks, network nodes, base stations, controllers, wireless devices, relay stations, and/or any other components or systems that may facilitate or participate in the communication of data and/or signals whether via wired or wireless connections.

As used herein, network node refers to equipment capable, configured, arranged and/or operable to communicate directly or indirectly with a wireless device and/or with other network nodes or equipment in the wireless network to enable and/or provide wireless access to the wireless device and/or to perform other functions (e.g., administration) in the wireless network. Examples of network nodes include, but are not limited to, access points (APs) (e.g., radio access points), base stations (BSs) (e.g., radio base stations, Node Bs, and evolved Node Bs (eNBs)). Base stations may be categorized based on the amount of coverage they provide (or, stated differently, their transmit power level) and may then also be referred to as femto base stations, pico base stations, micro base stations, or macro base stations. A base station may be a relay node or a relay donor node controlling a relay. A network node may also include one or more (or all) parts of a distributed radio base station such as centralized digital units and/or remote radio units (RRUs), sometimes referred to as Remote Radio Heads (RRHs). Such remote radio units may or may not be integrated with an antenna as an antenna integrated radio. Parts of a distributed radio base station may also be referred to as nodes in a distributed antenna system (DAS). Yet further examples of network nodes include multi-standard radio (MSR) equipment such as MSR BSs, network controllers such as radio network controllers (RNCs) or base station controllers (BSCs), base transceiver stations (BTSs), transmission points, transmission nodes, multi-cell/multicast coordination entities (MCEs), core network nodes and positioning nodes. As another example, a network node may be a virtual network node as described in more detail below. More generally, however, network nodes may represent any suitable device (or group of devices) capable, configured, arranged, and/or operable to enable and/or provide a wireless device with access to the wireless network or to provide some service to a wireless device that has accessed the wireless network.

In FIG. 1, network node 160 includes processing circuitry 170, device readable medium 180, interface 190, auxiliary equipment 184, power source 186, power circuitry 187, and antenna 162. Although network node 160 illustrated in the example wireless network of FIG. 1 may represent a device that includes the illustrated combination of hardware components, other embodiments may comprise network nodes with different combinations of components. It is to be understood that a network node comprises any suitable combination of hardware and/or software needed to perform the tasks, features, functions and methods disclosed herein. Moreover, while the components of network node 160 are depicted as single boxes located within a larger box, or nested within multiple boxes, in practice, a network node may comprise multiple different physical components that make up a single illustrated component (e.g., device readable medium 180 may comprise multiple separate hard drives as well as multiple RAM modules).

Similarly, network node 160 may be composed of multiple physically separate components (e.g., a NodeB component and an RNC component, or a BTS component and a BSC component, etc.), which may each have their own respective components. In certain scenarios in which network node 160 comprises multiple separate components (e.g., BTS and BSC components), one or more of the separate components may be shared among several network nodes. For example, a single RNC may control multiple NodeB's. In such a scenario, each unique NodeB and RNC pair, may in some instances be considered a single separate network node. In some embodiments, network node 160 may be configured to support multiple radio access technologies (RATs). In such embodiments, some components may be duplicated (e.g., separate device readable medium 180 for the different RATs) and some components may be reused (e.g., the same antenna 162 may be shared by the RATs). Network node 160 may also include multiple sets of the various illustrated components for different wireless technologies integrated into network node 160, such as, for example, GSM, WCDMA, LTE, NR, WiFi, or Bluetooth wireless technologies. These wireless technologies may be integrated into the same or different chip or set of chips and other components within network node 160.

Processing circuitry 170 is configured to perform any determining, calculating, or similar operations (e.g., certain obtaining operations) described herein as being provided by a network node. These operations performed by processing circuitry 170 may include processing information obtained by processing circuitry 170 by, for example, converting the obtained information into other information, comparing the obtained information or converted information to information stored in the network node, and/or performing one or more operations based on the obtained information or converted information, and as a result of said processing making a determination.

Processing circuitry 170 may comprise a combination of one or more of a microprocessor, controller, microcontroller, central processing unit, digital signal processor, application-specific integrated circuit, field programmable gate array, or any other suitable computing device, resource, or combination of hardware, software and/or encoded logic operable to provide, either alone or in conjunction with other network node 160 components, such as device readable medium 180, network node 160 functionality. For example, processing circuitry 170 may execute instructions stored in device readable medium 180 or in memory within processing circuitry 170. Such functionality may include providing any of the various wireless features, functions, or benefits discussed herein. In some embodiments, processing circuitry 170 may include a system on a chip (SOC).

In some embodiments, processing circuitry 170 may include one or more of radio frequency (RF) transceiver circuitry 172 and baseband processing circuitry 174. In some embodiments, RF transceiver circuitry 172 and baseband processing circuitry 174 may be on separate chips (or sets of chips), boards, or units, such as radio units and digital units. In alternative embodiments, part or all of RF transceiver circuitry 172 and baseband processing circuitry 174 may be on the same chip or set of chips, boards, or units In certain embodiments, some or all of the functionality described herein as being provided by a network node, base station, eNB or other such network device may be performed by processing circuitry 170 executing instructions stored on device readable medium 180 or memory within processing circuitry 170. In alternative embodiments, some or all of the functionality may be provided by processing circuitry 170 without executing instructions stored on a separate or discrete device readable medium, such as in a hard-wired manner. In any of those embodiments, whether executing instructions stored on a device readable storage medium or not, processing circuitry 170 can be configured to perform the described functionality. The benefits provided by such functionality are not limited to processing circuitry 170 alone or to other components of network node 160 but are enjoyed by network node 160 as a whole, and/or by end users and the wireless network generally.

Device readable medium 180 may comprise any form of volatile or non-volatile computer readable memory including, without limitation, persistent storage, solid-state memory, remotely mounted memory, magnetic media, optical media, random access memory (RAM), read-only memory (ROM), mass storage media (for example, a hard disk), removable storage media (for example, a flash drive, a Compact Disk (CD) or a Digital Video Disk (DVD)), and/or any other volatile or non-volatile, non-transitory device readable and/or computer-executable memory devices that store information, data, and/or instructions that may be used by processing circuitry 170. Device readable medium 180 may store any suitable instructions, data or information, including a computer program, software, an application including one or more of logic, rules, code, tables, etc. and/or other instructions capable of being executed by processing circuitry 170 and, utilized by network node 160. Device readable medium 180 may be used to store any calculations made by processing circuitry 170 and/or any data received via interface 190. In some embodiments, processing circuitry 170 and device readable medium 180 may be considered to be integrated.

Interface 190 is used in the wired or wireless communication of signalling and/or data between network node 160, network 106, and/or WDs 110. As illustrated, interface 190 comprises port(s)/terminal(s) 194 to send and receive data, for example to and from network 106 over a wired connection. Interface 190 also includes radio front end circuitry 192 that may be coupled to, or in certain embodiments a part of, antenna 162. Radio front end circuitry 192 comprises filters 198 and amplifiers 196. Radio front end circuitry 192 may be connected to antenna 162 and processing circuitry 170. Radio front end circuitry may be configured to condition signals communicated between antenna 162 and processing circuitry 170. Radio front end circuitry 192 may receive digital data that is to be sent out to other network nodes or WDs via a wireless connection. Radio front end circuitry 192 may convert the digital data into a radio signal having the appropriate channel and bandwidth parameters using a combination of filters 198 and/or amplifiers 196. The radio signal may then be transmitted via antenna 162. Similarly, when receiving data, antenna 162 may collect radio signals which are then converted into digital data by radio front end circuitry 192. The digital data may be passed to processing circuitry 170. In other embodiments, the interface may comprise different components and/or different combinations of components.

In certain alternative embodiments, network node 160 may not include separate radio front end circuitry 192, instead, processing circuitry 170 may comprise radio front end circuitry and may be connected to antenna 162 without separate radio front end circuitry 192. Similarly, in some embodiments, all or some of RF transceiver circuitry 172 may be considered a part of interface 190. In still other embodiments, interface 190 may include one or more ports or terminals 194, radio front end circuitry 192, and RF transceiver circuitry 172, as part of a radio unit (not shown), and interface 190 may communicate with baseband processing circuitry 174, which is part of a digital unit (not shown).

Antenna 162 may include one or more antennas, or antenna arrays, configured to send and/or receive wireless signals. Antenna 162 may be coupled to radio front end circuitry 190 and may be any type of antenna capable of transmitting and receiving data and/or signals wirelessly. In some embodiments, antenna 162 may comprise one or more omni-directional, sector or panel antennas operable to transmit/receive radio signals between, for example, 2 GHz and 66 GHz. An omni-directional antenna may be used to transmit/receive radio signals in any direction, a sector antenna may be used to transmit/receive radio signals from devices within a particular area, and a panel antenna may be a line of sight antenna used to transmit/receive radio signals in a relatively straight line. In some instances, the use of more than one antenna may be referred to as multiple-in-multiple-out (MIMO). In certain embodiments, antenna 162 may be separate from network node 160 and may be connectable to network node 160 through an interface or port.

Antenna 162, interface 190, and/or processing circuitry 170 may be configured to perform any receiving operations and/or certain obtaining operations described herein as being performed by a network node. Any information, data and/or signals may be received from a wireless device, another network node and/or any other network equipment. Similarly, antenna 162, interface 190, and/or processing circuitry 170 may be configured to perform any transmitting operations described herein as being performed by a network node. Any information, data and/or signals may be transmitted to a wireless device, another network node and/or any other network equipment.

Power circuitry 187 may comprise, or be coupled to, power management circuitry and is configured to supply the components of network node 160 with power for performing the functionality described herein. Power circuitry 187 may receive power from power source 186. Power source 186 and/or power circuitry 187 may be configured to provide power to the various components of network node 160 in a form suitable for the respective components (e.g., at a voltage and current level needed for each respective component). Power source 186 may either be included in, or external to, power circuitry 187 and/or network node 160. For example, network node 160 may be connectable to an external power source (e.g., an electricity outlet) via an input circuitry or interface such as an electrical cable, whereby the external power source supplies power to power circuitry 187. As a further example, power source 186 may comprise a source of power in the form of a battery or battery pack which is connected to, or integrated in, power circuitry 187. The battery may provide backup power should the external power source fail. Other types of power sources, such as photovoltaic devices, may also be used.

Alternative embodiments of network node 160 may include additional components beyond those shown in FIG. 1 that may be responsible for providing certain aspects of the network node's functionality, including any of the functionality described herein and/or any functionality necessary to support the subject matter described herein. For example, network node 160 may include user interface equipment to allow input of information into network node 160 and to allow output of information from network node 160. This may allow a user to perform diagnostic, maintenance, repair, and other administrative functions for network node 160.

As used herein, wireless device (WD) refers to a device capable, configured, arranged and/or operable to communicate wirelessly with network nodes and/or other wireless devices. Unless otherwise noted, the term WD may be used interchangeably herein with user equipment (UE). Communicating wirelessly may involve transmitting and/or receiving wireless signals using electromagnetic waves, radio waves, infrared waves, and/or other types of signals suitable for conveying information through air. In some embodiments, a WD may be configured to transmit and/or receive information without direct human interaction. For instance, a WD may be designed to transmit information to a network on a predetermined schedule, when triggered by an internal or external event, or in response to requests from the network. Examples of a WD include, but are not limited to, a smart phone, a mobile phone, a cell phone, a voice over IP (VoIP) phone, a wireless local loop phone, a desktop computer, a personal digital assistant (PDA), a wireless cameras, a gaming console or device, a music storage device, a playback appliance, a wearable terminal device, a wireless endpoint, a mobile station, a tablet, a laptop, a laptop-embedded equipment (LEE), a laptop-mounted equipment (LME), a smart device, a wireless customer-premise equipment (CPE). a vehicle-mounted wireless terminal device, etc. A WD may support device-to-device (D2D) communication, for example by implementing a 3GPP standard for sidelink communication, and may in this case be referred to as a D2D communication device. As yet another specific example, in an Internet of Things (IoT) scenario, a WD may represent a machine or other device that performs monitoring and/or measurements, and transmits the results of such monitoring and/or measurements to another WD and/or a network node. The WD may in this case be a machine-to-machine (M2M) device, which may in a 3GPP context be referred to as a machine-type communication (MTC) device. As one particular example, the WD may be a UE implementing the 3GPP narrow band internet of things (NB-IoT) standard. Particular examples of such machines or devices are sensors, metering devices such as power meters, industrial machinery, or home or personal appliances (e.g. refrigerators, televisions, etc.) personal wearables (e.g., watches, fitness trackers, etc.). In other scenarios, a WD may represent a vehicle or other equipment that is capable of monitoring and/or reporting on its operational status or other functions associated with its operation. A WD as described above may represent the endpoint of a wireless connection, in which case the device may be referred to as a wireless terminal. Furthermore, a WD as described above may be mobile, in which case it may also be referred to as a mobile device or a mobile terminal.

As illustrated, wireless device 110 includes antenna 111, interface 114, processing circuitry 120, device readable medium 130, user interface equipment 132, auxiliary equipment 134, power source 136 and power circuitry 137. WD 110 may include multiple sets of one or more of the illustrated components for different wireless technologies supported by WD 110, such as, for example, GSM, WCDMA, LTE, NR, WiFi, WiMAX, or Bluetooth wireless technologies, just to mention a few. These wireless technologies may be integrated into the same or different chips or set of chips as other components within WD 110.

Antenna 111 may include one or more antennas or antenna arrays, configured to send and/or receive wireless signals, and is connected to interface 114. In certain alternative embodiments, antenna 111 may be separate from WD 110 and be connectable to WD 110 through an interface or port. Antenna 111, interface 114, and/or processing circuitry 120 may be configured to perform any receiving or transmitting operations described herein as being performed by a WD. Any information, data and/or signals may be received from a network node and/or another WD. In some embodiments, radio front end circuitry and/or antenna 111 may be considered an interface.

As illustrated, interface 114 comprises radio front end circuitry 112 and antenna 111. Radio front end circuitry 112 comprise one or more filters 118 and amplifiers 116. Radio front end circuitry 114 is connected to antenna 111 and processing circuitry 120, and is configured to condition signals communicated between antenna 111 and processing circuitry 120. Radio front end circuitry 112 may be coupled to or a part of antenna 111. In some embodiments, WD 110 may not include separate radio front end circuitry 112; rather, processing circuitry 120 may comprise radio front end circuitry and may be connected to antenna 111. Similarly, in some embodiments, some or all of RF transceiver circuitry 122 may be considered a part of interface 114. Radio front end circuitry 112 may receive digital data that is to be sent out to other network nodes or WDs via a wireless connection. Radio front end circuitry 112 may convert the digital data into a radio signal having the appropriate channel and bandwidth parameters using a combination of filters 118 and/or amplifiers 116. The radio signal may then be transmitted via antenna 111. Similarly, when receiving data, antenna 111 may collect radio signals which are then converted into digital data by radio front end circuitry 112. The digital data may be passed to processing circuitry 120. In other embodiments, the interface may comprise different components and/or different combinations of components.

Processing circuitry 120 may comprise a combination of one or more of a microprocessor, controller, microcontroller, central processing unit, digital signal processor, application-specific integrated circuit, field programmable gate array, or any other suitable computing device, resource, or combination of hardware, software, and/or encoded logic operable to provide, either alone or in conjunction with other WD 110 components, such as device readable medium 130, WD 110 functionality. Such functionality may include providing any of the various wireless features or benefits discussed herein.

For example, processing circuitry 120 may execute instructions stored in device readable medium 130 or in memory within processing circuitry 120 to provide the functionality disclosed herein.

As illustrated, processing circuitry 120 includes one or more of RF transceiver circuitry 122, baseband processing circuitry 124, and application processing circuitry 126. In other embodiments, the processing circuitry may comprise different components and/or different combinations of components. In certain embodiments processing circuitry 120 of WD 110 may comprise a SOC. In some embodiments, RF transceiver circuitry 122, baseband processing circuitry 124, and application processing circuitry 126 may be on separate chips or sets of chips. In alternative embodiments, part or all of baseband processing circuitry 124 and application processing circuitry 126 may be combined into one chip or set of chips, and RF transceiver circuitry 122 may be on a separate chip or set of chips. In still alternative embodiments, part or all of RF transceiver circuitry 122 and baseband processing circuitry 124 may be on the same chip or set of chips, and application processing circuitry 126 may be on a separate chip or set of chips. In yet other alternative embodiments, part or all of RF transceiver circuitry 122, baseband processing circuitry 124, and application processing circuitry 126 may be combined in the same chip or set of chips. In some embodiments, RF transceiver circuitry 122 may be a part of interface 114. RF transceiver circuitry 122 may condition RF signals for processing circuitry 120.

In certain embodiments, some or all of the functionality described herein as being performed by a WD may be provided by processing circuitry 120 executing instructions stored on device readable medium 130, which in certain embodiments may be a computer-readable storage medium. In alternative embodiments, some or all of the functionality may be provided by processing circuitry 120 without executing instructions stored on a separate or discrete device readable storage medium, such as in a hard-wired manner. In any of those particular embodiments, whether executing instructions stored on a device readable storage medium or not, processing circuitry 120 can be configured to perform the described functionality. The benefits provided by such functionality are not limited to processing circuitry 120 alone or to other components of WD 110, but are enjoyed by WD 110 as a whole, and/or by end users and the wireless network generally.

Processing circuitry 120 may be configured to perform any determining, calculating, or similar operations (e.g., certain obtaining operations) described herein as being performed by a WD. These operations, as performed by processing circuitry 120, may include processing information obtained by processing circuitry 120 by, for example, converting the obtained information into other information, comparing the obtained information or converted information to information stored by WD 110, and/or performing one or more operations based on the obtained information or converted information, and as a result of said processing making a determination.

Device readable medium 130 may be operable to store a computer program, software, an application including one or more of logic, rules, code, tables, etc. and/or other instructions capable of being executed by processing circuitry 120. Device readable medium 130 may include computer memory (e.g., Random Access Memory (RAM) or Read Only Memory (ROM)), mass storage media (e.g., a hard disk), removable storage media (e.g., a Compact Disk (CD) or a Digital Video Disk (DVD)), and/or any other volatile or non-volatile, non-transitory device readable and/or computer executable memory devices that store information, data, and/or instructions that may be used by processing circuitry 120. In some embodiments, processing circuitry 120 and device readable medium 130 may be considered to be integrated.

User interface equipment 132 may provide components that allow for a human user to interact with WD 110. Such interaction may be of many forms, such as visual, audial, tactile, etc. User interface equipment 132 may be operable to produce output to the user and to allow the user to provide input to WD 110. The type of interaction may vary depending on the type of user interface equipment 132 installed in WD 110. For example, if WD 110 is a smart phone, the interaction may be via a touch screen; if WD 110 is a smart meter, the interaction may be through a screen that provides usage (e.g., the number of gallons used) or a speaker that provides an audible alert (e.g., if smoke is detected). User interface equipment 132 may include input interfaces, devices and circuits, and output interfaces, devices and circuits. User interface equipment 132 is configured to allow input of information into WD 110, and is connected to processing circuitry 120 to allow processing circuitry 120 to process the input information. User interface equipment 132 may include, for example, a microphone, a proximity or other sensor, keys/buttons, a touch display, one or more cameras, a USB port, or other input circuitry. User interface equipment 132 is also configured to allow output of information from WD 110, and to allow processing circuitry 120 to output information from WD 110. User interface equipment 132 may include, for example, a speaker, a display, vibrating circuitry, a USB port, a headphone interface, or other output circuitry. Using one or more input and output interfaces, devices, and circuits, of user interface equipment 132, WD 110 may communicate with end users and/or the wireless network, and allow them to benefit from the functionality described herein.

Auxiliary equipment 134 is operable to provide more specific functionality which may not be generally performed by WDs. This may comprise specialized sensors for doing measurements for various purposes, interfaces for additional types of communication such as wired communications etc. The inclusion and type of components of auxiliary equipment 134 may vary depending on the embodiment and/or scenario.

Power source 136 may, in some embodiments, be in the form of a battery or battery pack. Other types of power sources, such as an external power source (e.g., an electricity outlet), photovoltaic devices or power cells, may also be used. WD 110 may further comprise power circuitry 137 for delivering power from power source 136 to the various parts of WD 110 which need power from power source 136 to carry out any functionality described or indicated herein. Power circuitry 137 may in certain embodiments comprise power management circuitry. Power circuitry 137 may additionally or alternatively be operable to receive power from an external power source; in which case WD 110 may be connectable to the external power source (such as an electricity outlet) via input circuitry or an interface such as an electrical power cable. Power circuitry 137 may also in certain embodiments be operable to deliver power from an external power source to power source 136. This may be, for example, for the charging of power source 136. Power circuitry 137 may perform any formatting, converting, or other modification to the power from power source 136 to make the power suitable for the respective components of WD 110 to which power is supplied.

According to some embodiments, WD 110 is a UE and the UE is configured in an uplink split-bearer configuration to transmit PDUs by a first RLC entity via a first uplink transmission path and/or by a second RLC entity via a second uplink transmission path. The processing circuitry 120 of the UE is configured to determine a total amount of data volume buffered for PDU transmission, where the total amount of data volume includes the PDCP data volume and data that has been moved from PDCP to the first and/or second RLC entities for pre-processing and for which a grant of uplink resources has not been received (RLC data volume pending for initial transmission in the two RLC entities). The processing circuitry is also configured to report the PDCP data volume to at least the first uplink transmission path, based on whether the total amount of data volume meets or exceeds a first threshold. The reporting includes, in response to determining that the total amount of data volume meets or exceeds the first threshold, indicating the PDCP data volume to both the first uplink transmission path and the second uplink transmission path, and, in response to determining that the total amount of data volume does not meet the first threshold, indicating the PDCP data volume to only the first uplink transmission path.

The first uplink transmission path may be configured as a prioritized uplink transmission path and the second uplink transmission path may be configured as an unprioritized uplink transmission path. The first RLC entity may belong to an MCG, and the second RLC entity may belong to a SCG.

Figure 2:
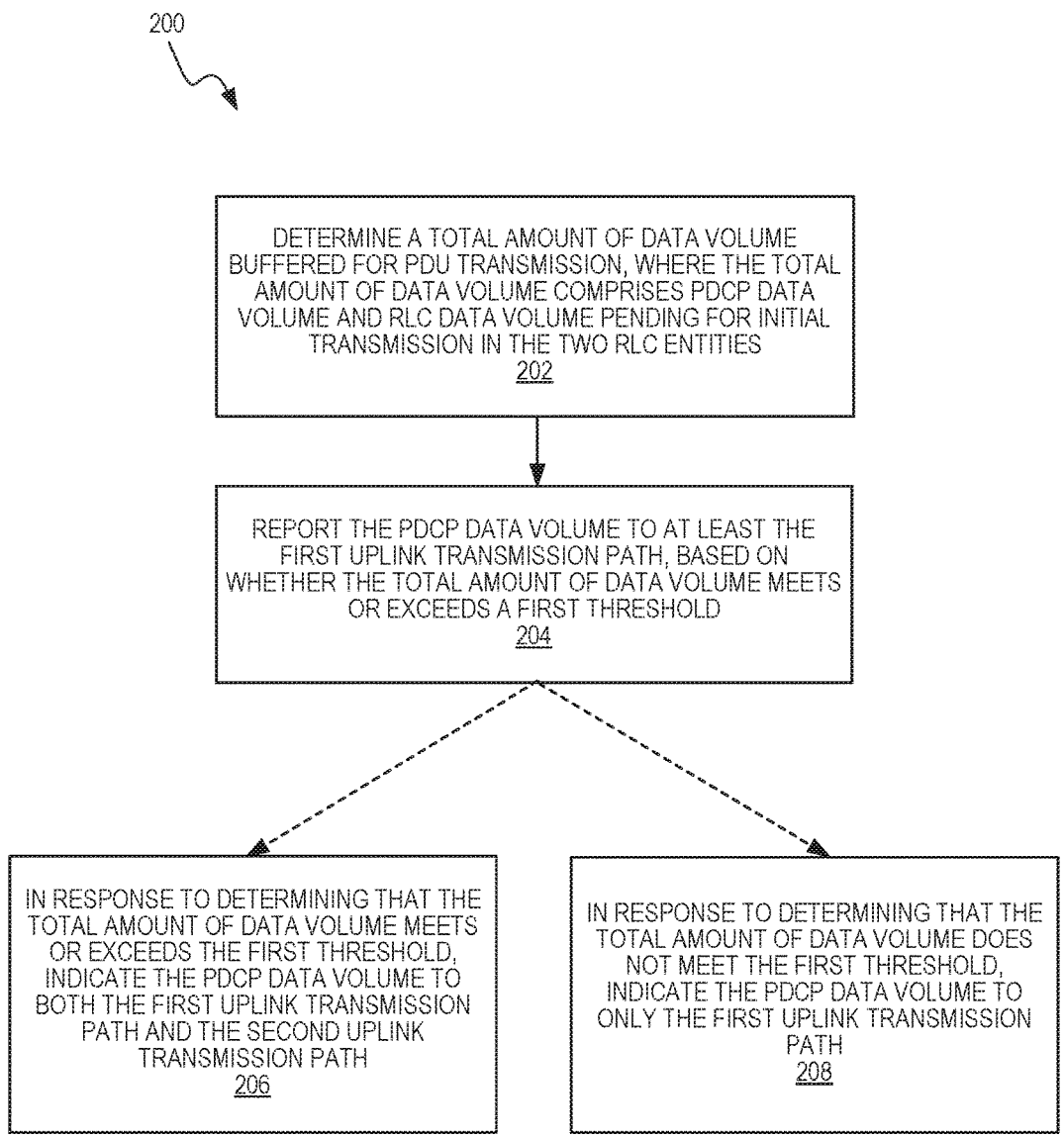
FIG. 2 is a flowchart illustrating a method carried out by a UE, according to some embodiments.

In some embodiments, the processing circuitry 120 is configured to perform a corresponding method, such as method 200 shown in FIG. 2, in a UE that is configured in an uplink split-bearer configuration to transmit PDUs by a first RLC entity via a first uplink transmission path and/or by a second RLC entity via a second uplink transmission path. The method 200 includes determining a total amount of data buffered for PDU transmission (block 202). The total amount of data includes PDCP data volume and RLC data volume pending for initial transmission in the two RLC entities. The method 200 also includes reporting the PDCP data volume to at least the first uplink transmission path, based on whether the total amount of data volume meets or exceeds a first threshold (block 204). The reporting includes, in response to determining that the total amount of data volume meets or exceeds the first threshold, indicating the PDCP data volume to both the first uplink transmission path and the second uplink transmission path (block 206), and, in response to determining that the total amount of data volume does not meet the first threshold, indicating the PDCP data volume to only the first uplink transmission path (block 208).

The method 200 may also include, in response to determining that the total amount of data volume does not meet the first threshold, submitting the PDCP data volume only to the first RLC entity.

According to further embodiments, the processing circuitry 120 of the UE is configured to determine a total amount of data volume buffered for PDU transmission, where the total amount of data volume includes PDCP data volume and RLC data volume pending for initial transmission in the two RLC entities. The processing circuitry 120 is also configured to decide whether submission of the PDCP data volume is allowed to either of the two RLC entities or to only the first RLC entity, based on whether the total amount of data volume meets or exceeds a first threshold. The deciding includes, in response to determining that the total amount of data volume meets or exceeds the first threshold, deciding that the PDCP data volume is allowed to be submitted to either of the two RLC entities, and, in response to determining that the total amount of data volume does not meet the first threshold, deciding that the PDCP data volume is allowed to be submitted to only the first RLC entity.

According to certain embodiments, the first uplink transmission path corresponds to a MAC entity associated with the first RLC entity, and the second uplink transmission path corresponds to a MAC entity associated with the second RLC entity.

Figure 3:
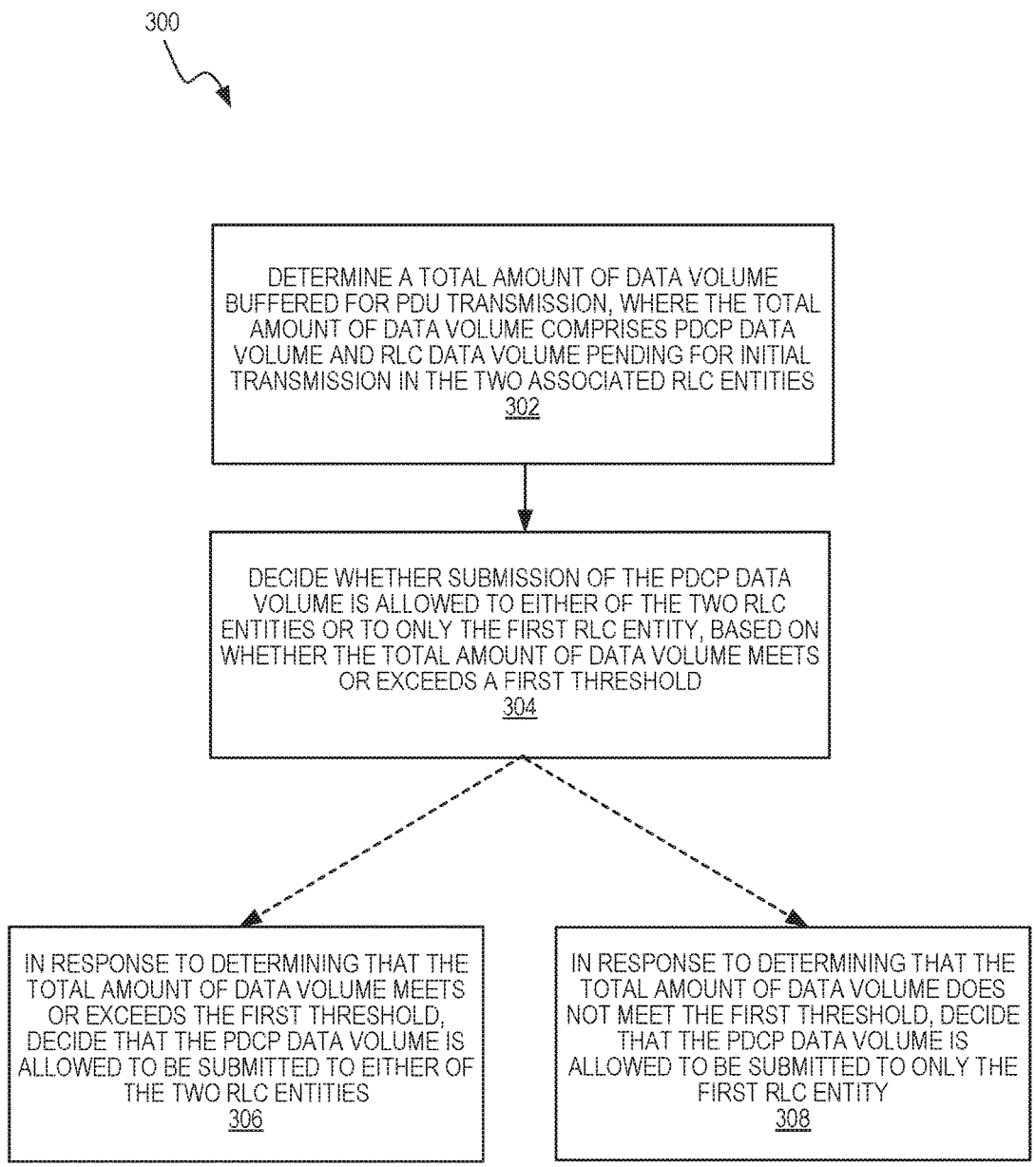
FIG. 3 is a flowchart illustrating another method carried out by a UE, according to some embodiments.

In some embodiments, the processing circuitry 120 is configured to perform a corresponding method, such as method 300 shown in FIG. 3, in a UE that is configured in an uplink split-bearer configuration to transmit PDUs by a first RLC entity via a first uplink transmission path and/or by a second RLC entity via a second uplink transmission path. The method 300 includes determining a total amount of data buffered for PDU transmission (block 302). The total amount of data includes PDCP data volume and RLC data volume pending for initial transmission in the two RLC entities. The method 300 also includes deciding whether submission of the PDCP data volume is allowed to either of the two RLC entities or to only the first RLC entity, based on whether the total amount of data volume meets or exceeds a first threshold (block 304). The deciding includes, in response to determining that the total amount of data volume meets or exceeds the first threshold, deciding that the PDCP data volume is allowed to be submitted to either of the two RLC entities (block 306), and, in response to determining that the total amount of data volume does not meet the first threshold, deciding that the PDCP data volume is allowed to be submitted to only the first RLC entity (block 308).

The method may further include submitting the PDCP data volume according to the decision. The method may include, in response to deciding that the PDCP data volume is allowed to be submitted to either of the two RLC entities, submitting the PDCP data volume to whichever of the two RLC entities requested the PDCP data volume.

According to certain embodiments, the first uplink transmission path corresponds to a MAC entity associated with the first RLC entity, and the second uplink transmission path corresponds to a MAC entity associated with the second RLC entity.

Figure 4:
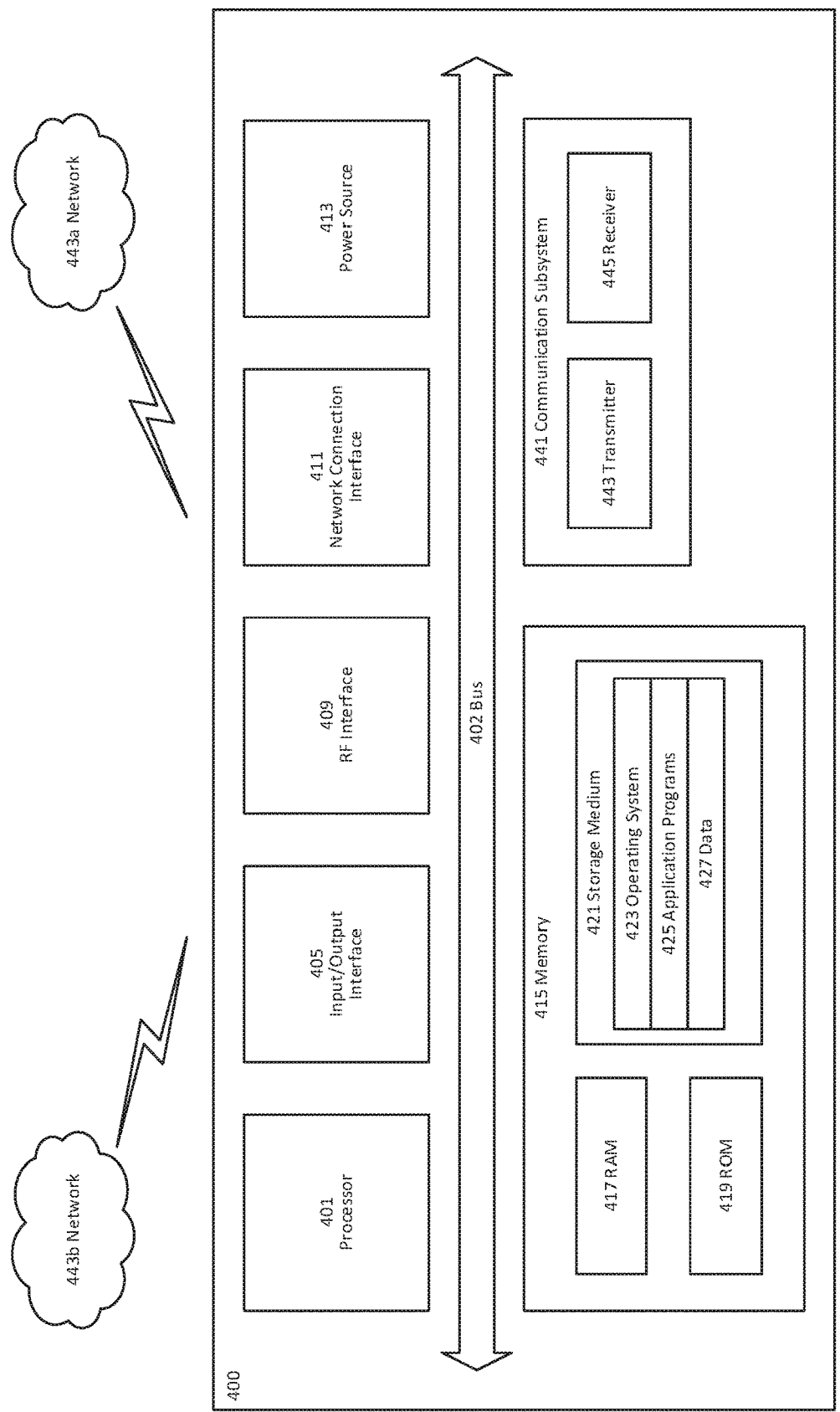
FIG. 4 is a block diagram of a UE, according to some embodiments.

FIG. 4 illustrates one embodiment of a UE in accordance with various aspects described herein. As used herein, a user equipment or UE may not necessarily have a user in the sense of a human user who owns and/or operates the relevant device. Instead, a UE may represent a device that is intended for sale to, or operation by, a human user but which may not, or which may not initially, be associated with a specific human user. A UE may also comprise any UE identified by the 3rd Generation Partnership Project (3GPP), including a NB-IoT UE that is not intended for sale to, or operation by, a human user. UE 400, as illustrated in FIG. 4, is one example of a WD configured for communication in accordance with one or more communication standards promulgated by the 3rd Generation Partnership Project (3GPP), such as 3GPP's GSM, UMTS, LTE, and/or 5G standards. As mentioned previously, the term WD and UE may be used interchangeable. Accordingly, although FIG. 4 is a UE, the components discussed herein are equally applicable to a WD, and vice-versa.

In FIG. 4, UE 400 includes processing circuitry 401 that is operatively coupled to input/output interface 405, radio frequency (RF) interface 409, network connection interface 411, memory 415 including random access memory (RAM) 417, read-only memory (ROM) 419, and storage medium 421 or the like, communication subsystem 441, power source 433, and/or any other component, or any combination thereof. Storage medium 421 includes operating system 423, application program 425, and data 427. In other embodiments, storage medium 421 may include other similar types of information. Certain UEs may utilize all of the components shown in FIG. 4, or only a subset of the components. The level of integration between the components may vary from one UE to another UE. Further, certain UEs may contain multiple instances of a component, such as multiple processors, memories, transceivers, transmitters, receivers, etc.

In FIG. 4, processing circuitry 401 may be configured to process computer instructions and data. Processing circuitry 401 may be configured to implement any sequential state machine operative to execute machine instructions stored as machine-readable computer programs in the memory, such as one or more hardware-implemented state machines (e.g., in discrete logic, FPGA, ASIC, etc.); programmable logic together with appropriate firmware; one or more stored program, general-purpose processors, such as a microprocessor or Digital Signal Processor (DSP), together with appropriate software; or any combination of the above. For example, the processing circuitry 401 may include two central processing units (CPUs). Data may be information in a form suitable for use by a computer.

In the depicted embodiment, input/output interface 405 may be configured to provide a communication interface to an input device, output device, or input and output device. UE 400 may be configured to use an output device via input/output interface 405. An output device may use the same type of interface port as an input device. For example, a USB port may be used to provide input to and output from UE 400. The output device may be a speaker, a sound card, a video card, a display, a monitor, a printer, an actuator, an emitter, a smartcard, another output device, or any combination thereof. UE 400 may be configured to use an input device via input/output interface 405 to allow a user to capture information into UE 400. The input device may include a touch-sensitive or presence-sensitive display, a camera (e.g., a digital camera, a digital video camera, a web camera, etc.), a microphone, a sensor, a mouse, a trackball, a directional pad, a trackpad, a scroll wheel, a smartcard, and the like. The presence-sensitive display may include a capacitive or resistive touch sensor to sense input from a user. A sensor may be, for instance, an accelerometer, a gyroscope, a tilt sensor, a force sensor, a magnetometer, an optical sensor, a proximity sensor, another like sensor, or any combination thereof. For example, the input device may be an accelerometer, a magnetometer, a digital camera, a microphone, and an optical sensor.

In FIG. 4, RF interface 409 may be configured to provide a communication interface to RF components such as a transmitter, a receiver, and an antenna. Network connection interface 411 may be configured to provide a communication interface to network 443a. Network 443a may encompass wired and/or wireless networks such as a local-area network (LAN), a wide-area network (WAN), a computer network, a wireless network, a telecommunications network, another like network or any combination thereof. For example, network 443a may comprise a Wi-Fi network. Network connection interface 411 may be configured to include a receiver and a transmitter interface used to communicate with one or more other devices over a communication network according to one or more communication protocols, such as Ethernet, TCP/IP, SONET, ATM, or the like. Network connection interface 411 may implement receiver and transmitter functionality appropriate to the communication network links (e.g., optical, electrical, and the like). The transmitter and receiver functions may share circuit components, software or firmware, or alternatively may be implemented separately.

RAM 417 may be configured to interface via bus 402 to processing circuitry 401 to provide storage or caching of data or computer instructions during the execution of software programs such as the operating system, application programs, and device drivers. ROM 419 may be configured to provide computer instructions or data to processing circuitry 401. For example, ROM 419 may be configured to store invariant low-level system code or data for basic system functions such as basic input and output (I/O), startup, or reception of keystrokes from a keyboard that are stored in a non-volatile memory. Storage medium 421 may be configured to include memory such as RAM, ROM, programmable read-only memory (PROM), erasable programmable read-only memory (EPROM), electrically erasable programmable read-only memory (EEPROM), magnetic disks, optical disks, floppy disks, hard disks, removable cartridges, or flash drives. In one example, storage medium 421 may be configured to include operating system 423, application program 425 such as a web browser application, a widget or gadget engine or another application, and data file 427. Storage medium 421 may store, for use by UE 400, any of a variety of various operating systems or combinations of operating systems.

Storage medium 421 may be configured to include a number of physical drive units, such as redundant array of independent disks (RAID), floppy disk drive, flash memory, USB flash drive, external hard disk drive, thumb drive, pen drive, key drive, high-density digital versatile disc (HD-DVD) optical disc drive, internal hard disk drive, Blu-Ray optical disc drive, holographic digital data storage (HDDS) optical disc drive, external mini-dual in-line memory module (DIMM), synchronous dynamic random access memory (SDRAM), external micro-DIMM SDRAM, smartcard memory such as a subscriber identity module or a removable user identity (SIM/RUIM) module, other memory, or any combination thereof. Storage medium 421 may allow UE 400 to access computer-executable instructions, application programs or the like, stored on transitory or non-transitory memory media, to off-load data, or to upload data. An article of manufacture, such as one utilizing a communication system may be tangibly embodied in storage medium 421, which may comprise a device readable medium.

In FIG. 4, processing circuitry 401 may be configured to communicate with network 443b using communication subsystem 431. Network 443a and network 443b may be the same network or networks or different network or networks. Communication subsystem 431 may be configured to include one or more transceivers used to communicate with network 443b. For example, communication subsystem 431 may be configured to include one or more transceivers used to communicate with one or more remote transceivers of another device capable of wireless communication such as another WD, UE, or base station of a radio access network (RAN) according to one or more communication protocols, such as IEEE 802.2, CDMA, WCDMA, GSM, LTE, UTRAN, WiMax, or the like. Each transceiver may include transmitter 433 and/or receiver 435 to implement transmitter or receiver functionality, respectively, appropriate to the RAN links (e.g., frequency allocations and the like). Further, transmitter 433 and receiver 435 of each transceiver may share circuit components, software or firmware, or alternatively may be implemented separately.

In the illustrated embodiment, the communication functions of communication subsystem 431 may include data communication, voice communication, multimedia communication, short-range communications such as Bluetooth, near-field communication, location-based communication such as the use of the global positioning system (GPS) to determine a location, another like communication function, or any combination thereof. For example, communication subsystem 431 may include cellular communication, Wi-Fi communication, Bluetooth communication, and GPS communication. Network 443b may encompass wired and/or wireless networks such as a local-area network (LAN), a wide-area network (WAN), a computer network, a wireless network, a telecommunications network, another like network or any combination thereof. For example, network 443b may be a cellular network, a Wi-Fi network, and/or a near-field network. Power source 413 may be configured to provide alternating current (AC) or direct current (DC) power to components of UE 400.

The features, benefits and/or functions described herein may be implemented in one of the components of UE 400 or partitioned across multiple components of UE 400. Further, the features, benefits, and/or functions described herein may be implemented in any combination of hardware, software or firmware. In one example, communication subsystem 431 may be configured to include any of the components described herein. Further, processing circuitry 401 may be configured to communicate with any of such components over bus 402. In another example, any of such components may be represented by program instructions stored in memory that when executed by processing circuitry 401 perform the corresponding functions described herein. In another example, the functionality of any of such components may be partitioned between processing circuitry 401 and communication subsystem 431. In another example, the non-computationally intensive functions of any of such components may be implemented in software or firmware and the computationally intensive functions may be implemented in hardware.

Figure 5:
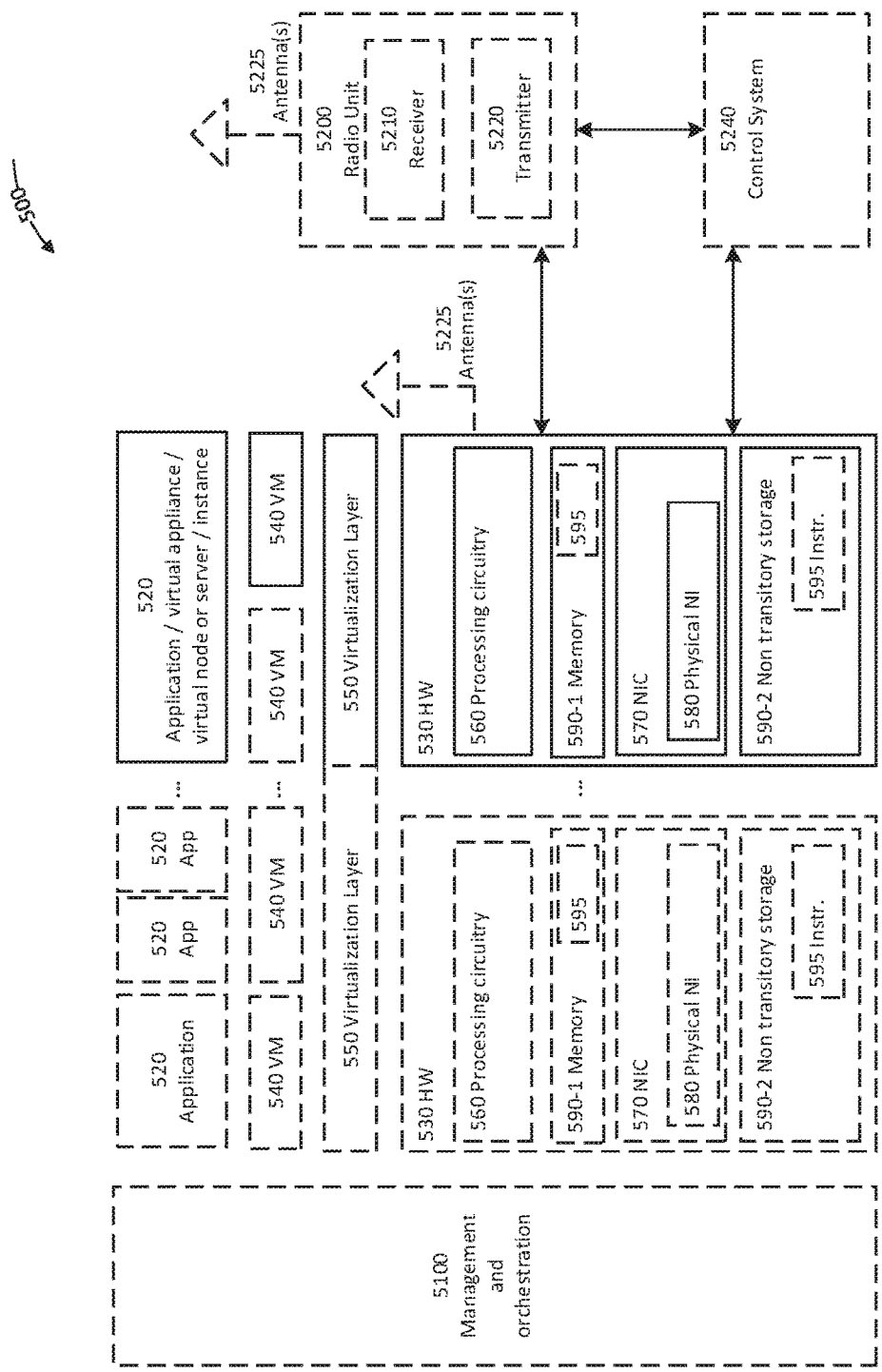
FIG. 5 illustrates a virtualization environment, according to some embodiments.

FIG. 5 is a schematic block diagram illustrating a virtualization environment 500 in which functions implemented by some embodiments may be virtualized. In the present context, virtualizing means creating virtual versions of apparatuses or devices which may include virtualizing hardware platforms, storage devices and networking resources. As used herein, virtualization can be applied to a node (e.g., a virtualized base station or a virtualized radio access node) or to a device (e.g., a UE, a wireless device or any other type of communication device) or components thereof and relates to an implementation in which at least a portion of the functionality is implemented as one or more virtual components (e.g., via one or more applications, components, functions, virtual machines or containers executing on one or more physical processing nodes in one or more networks).

In some embodiments, some or all of the functions described herein may be implemented as virtual components executed by one or more virtual machines implemented in one or more virtual environments 500 hosted by one or more of hardware nodes 530. Further, in embodiments in which the virtual node is not a radio access node or does not require radio connectivity (e.g., a core network node), then the network node may be entirely virtualized.

The functions may be implemented by one or more applications 520 (which may alternatively be called software instances, virtual appliances, network functions, virtual nodes, virtual network functions, etc.) operative to implement some of the features, functions, and/or benefits of some of the embodiments disclosed herein. Applications 520 are run in virtualization environment 500 which provides hardware 530 comprising processing circuitry 560 and memory 590. Memory 590 contains instructions 595 executable by processing circuitry 560 whereby application 520 is operative to provide one or more of the features, benefits, and/or functions disclosed herein.

Virtualization environment 500, comprises general-purpose or special-purpose network hardware devices 530 comprising a set of one or more processors or processing circuitry 560, which may be commercial off-the-shelf (COTS) processors, dedicated Application Specific Integrated Circuits (ASICs), or any other type of processing circuitry including digital or analog hardware components or special purpose processors. Each hardware device may comprise memory 590-1 which may be non-persistent memory for temporarily storing instructions 595 or software executed by processing circuitry 560. Each hardware device may comprise one or more network interface controllers (NICs) 570, also known as network interface cards, which include physical network interface 580. Each hardware device may also include non-transitory, persistent, machine-readable storage media 590-2 having stored therein software 595 and/or instructions executable by processing circuitry 560. Software 595 may include any type of software including software for instantiating one or more virtualization layers 550 (also referred to as hypervisors), software to execute virtual machines 540 as well as software allowing it to execute functions, features and/or benefits described in relation with some embodiments described herein.

Virtual machines 540, comprise virtual processing, virtual memory, virtual networking or interface and virtual storage, and may be run by a corresponding virtualization layer 550 or hypervisor. Different embodiments of the instance of virtual appliance 520 may be implemented on one or more of virtual machines 540, and the implementations may be made in different ways.

During operation, processing circuitry 560 executes software 595 to instantiate the hypervisor or virtualization layer 550, which may sometimes be referred to as a virtual machine monitor (VMM). Virtualization layer 550 may present a virtual operating platform that appears like networking hardware to virtual machine 540.

As shown in FIG. 5, hardware 530 may be a standalone network node with generic or specific components. Hardware 530 may comprise antenna 5225 and may implement some functions via virtualization. Alternatively, hardware 530 may be part of a larger cluster of hardware (e.g. such as in a data center or customer premise equipment (CPE)) where many hardware nodes work together and are managed via management and orchestration (MANO) 5100, which, among others, oversees lifecycle management of applications 520.

Virtualization of the hardware is in some contexts referred to as network function virtualization (NFV). NFV may be used to consolidate many network equipment types onto industry standard high volume server hardware, physical switches, and physical storage, which can be located in data centers, and customer premise equipment.

In the context of NFV, virtual machine 540 may be a software implementation of a physical machine that runs programs as if they were executing on a physical, non-virtualized machine. Each of virtual machines 540, and that part of hardware 530 that executes that virtual machine, be it hardware dedicated to that virtual machine and/or hardware shared by that virtual machine with others of the virtual machines 540, forms a separate virtual network elements (VNE).

Still in the context of NFV, Virtual Network Function (VNF) is responsible for handling specific network functions that run in one or more virtual machines 540 on top of hardware networking infrastructure 530 and corresponds to application 520 in FIG. 5.

In some embodiments, one or more radio units 5200 that each include one or more transmitters 5220 and one or more receivers 5210 may be coupled to one or more antennas 5225. Radio units 5200 may communicate directly with hardware nodes 530 via one or more appropriate network interfaces and may be used in combination with the virtual components to provide a virtual node with radio capabilities, such as a radio access node or a base station.

In some embodiments, some signalling can be affected with the use of control system 5240 which may alternatively be used for communication between the hardware nodes 530 and radio units 5200.

Embodiments described herein can also avoid what can be described as "bad" UE behaviour by limiting UE-based pre-processing, or the processing of PDCP PDUs in RLC entities at the RLC layer that create RLC PDUs before an uplink grant is received. Some issues need to be addressed in order to avoid this bad UE behaviour. One issue may be that the pre-processing is not being performed according to a specified grant ratio, leading to reordering delays. Another issue may be that the pre-processed data for one uplink direction may get stuck when no further grant can be issued, leading to eventual data loss. Given these issues, it becomes clear that because the UE cannot estimate the gNB's scheduling behavior entirely (the UE does not know the grant size or ratio among transmission paths), leaving the level of pre-processing in an uplink split bearer configuration to the UE may not be feasible.

Some embodiments described herein limit the amount of PDU pre-processing by the UE that may exhibit bad UE behaviour, whether the pre-processing is too extensive and/or not according to the specified uplink grant ratio. For example, the maximum time until a transmission gap is closed by the transmitter may be limited. A transmission gap might be introduced by the UE by sending PDU sequence number (SN) n+1 via one path, while sending PDU SN n via the other path. A transmission gap is created in this case, when PDU n+1 is transmitted before PDU n, which might happen when a grant for PDU n+1 becomes available earlier than for PDU n. The UE is mandated to close the transmission gap within a configurable time.

The pre-processing at the UE can be limited in a number of ways. In one example, the maximum transmission time difference among uplink transmission paths/legs/RLC-entities/cell groups of subsequent PDCP PDUs may be limited. The maximum transmission time difference may be the time until a transmission gap is to be closed (among transmissions on different uplink paths). The pre-processing may be limited by a maximum buffering/queueing time on one RLC entity, while transmission of a previous/subsequent PDCP PDU takes place on other RLC entity. In another example, pre-processing may take place until a transmitter side reordering timer expires, the timer being started when a transmission gap is introduced and stopped when the transmission gap is closed.

To avoid pre-processing that is too extensive, such as when a maximum pre-processing time is about to be reached or when a timer expires, the UE has to re-pre-process the data to be transmitted in the other RLC entity, i.e., on the other uplink path. The UE may do so before a maximum time is reached or a timer expires, since the re-pre-processing also takes some time. In an example, the maximum time to close a transmission gap is 5 ms, but re-pre-processing takes 2 ms. In this case, the UE would, when a transmission gap exists for 3 ms, decide to re-pre-process the PDU waiting for transmission in one RLC associated with a first uplink transmission path, to be ready for transmission in the other RLC entity associated with the second uplink transmission path. If a transmission queue of data exists in this other RLC, the UE might do the additional pre-processing (re-pre-processing) even earlier to consider this queue delay there as well. Alternatively, the UE may re-pre-process the PDU to be transmitted as the first element of the transmission queue (put it in front of the queue).

The re-pre-processing of the PDCP PDU may undergo several steps. The steps may include, in the old RLC entity, discarding the PDCP PDU (i.e., the RLC SDU and associated RLC PDUs), which can be achieved with the RLC SDU/PDU discard functionality, as specified in 3GPP TS 38.322. The PDCP PDU may be provided from RLC towards PDCP for handling there. The RLC discard step includes updating of the TX_NEXT state variable and re-pre-processing (header/SN assignment/update) of other RLC PDUs in the queue. In the case where the RLC SDU cannot be discarded (e.g., because at least one of the associated RLC PDUs has been already transmitted), the step above is skipped. This means that the RLC SDU is only discarded if no segment of the RLC SDU had already been submitted to lower layer for transmission.

The PDCP entity may still have a pointer/association with this PDU, or may receive it from the old RLC entity within the previous step. The PDCP may re-transmit the PDU towards the new RLC entity. In the new RLC entity, the PDCP PDU is pre-processed (i.e., an RLC PDU header/SN is assigned). The UE can put the PDU at the end of the queue. If the UE puts the PDU at the front of the queue (for earlier transmission), RLC PDU headers/SNs of subsequent (now shifted back) PDUs need to be updated accordingly.

There are two primary options to avoid these issues:
Option 1: Fully Specified Solution In a first option, according to some embodiments, data submission of PDCP PDUs to any lower layer is allowed at any time, when data is above the split threshold. To avoid excessive reordering delays, a maximum skew time may be specified. This can be done, for example, by a transmission reordering timer resembling a reception reordering timer. Data submission can also be performed with per-PDU timers counting the maximum transmission time difference of one PDU in relation to subsequent PDUs transmitted on another uplink transmission path or cell group.

To prevent pre-processed uplink data from getting stuck at expiry of such a timer, the RLC entity must discard the stuck pre-processed PDUs and proceed with retransmission operations. This may involve an RLC header/SN recalculation for subsequent data. TX_NEXT may need to be updated. This may also involve retransmission of the data via the other RLC entity. Ideally, these retransmissions are performed before other PDUs are pre-processed in this other RLC entity. That is, the data to be retransmitted may be added at the front of the queue, involving another RLC header/SN recalculation for subsequent data. Note that in some cases, the RLC might not be able to discard the stuck RLC SDU and associated RLC PDUs. This may be due to the fact that at least one associated RLC PDU has been already transmitted by the transmitter. Discarding the RLC SDU and associated PDUs will cause the receiver side to request retransmissions of those PDUs—if RLC Acknowledged Mode (AM) is used. For RLC Unacknowledged Mode (UM), however, it is possible to discard the RLC SDU and associated RLC PDUs without any risk. The timer implementation and discarding procedures can be foreseen on PDCP or on each RLC entity. The PDCP retransmission procedure may be standardized for the "reshuffling" of data between the RLC entities.

Option 2: Submission Upon Request Only, with Exception of Allowed Limited Pre-Processing In this approach, the LTE protocol design and modeling of submission to PDCP lower layers is inherited, including "submission upon-request only" for the split bearer. This way, no further specification impact to other procedures (e.g., discard, PDCP retransmissions, etc.) is needed.

To not preclude pre-processing in some implementations, transmission is allowed to lower layers beforehand, however restricted. To avoid bad UE behaviour stemming from the UE estimating the uplink grant ratios incorrectly, a pre-processing limit may need to be specified.

An effective way to avoid the above-mentioned issue is to allow pre-processing only on the condition that the potentially introduced jitter due to introduced transmission gaps is limited by a specified delay-threshold. Transmission gaps are, for example, introduced when the UE pre-processes data (e.g., PDCP PDU SN n) for transmission via the SN, while a subsequent PDU SN n+1 is transmitted via the MN.

According to certain embodiments, extensive pre-processing or pre-processing not in accordance with a UL grant ratio can be avoided by limiting the maximum time until a transmission gap is closed by the transmitter. This is the maximum time to transmit PDU n, if PDU n+1 was already transmitted. In some embodiments, the submission of PDCP PDUs is upon request from lower layers.

According to certain embodiments, as an exception to some of the above embodiments, submission of PDCP PDUs to lower layer RLC (for the purpose of pre-processing) is allowed under the condition that a potential transmission gap among the uplink transmission paths is closed within a specified time threshold.

According to certain embodiments, when the UE applies pre-processing, the UE is mandated to close a transmission gap within the specified time threshold. That is, the UE re-processes the PDCP PDU for transmission via the other transmission path or cell group. This way, the potential jitter introduced by UE-based uplink bearer splitting (pre-processing on different RLC entities) is limited. Furthermore, this limitation ensures network control of the radio resources to be used, i.e., the UE can pre-determine the uplink transmission path thus allowing pre-processing, but this does not mandate the network to issue an uplink grant on that path. Thereby, the UE, by ensuring that the reordering-depth (time to close gap) is below the threshold, implies also that the UE has to potentially re-process data from one uplink transmission path to another uplink transmission path (e.g., SCG RLC to MCG RLC)—in case it is pre-processed too aggressively and the uplink grant ratios are not estimated correctly. The re-processing can thereby take some time. The UE must only ensure the maximum reordering-depth (time to close the gap), which can be in the order of the maximum wanted jitter, e.g., 5 ms. While the interactions between the RLC entities (and PDCP) may be left to UE implementation, in the specified model, PDCP submits data to lower layers only upon request.

For example, the UE pre-processes an amount of data for estimated grant sizes on a master cell group (MCG) and a secondary cell group (SCG). In the case where the UE estimated the SCG grant size wrongly by a factor 10 higher than the actual grant size, it would introduce at the end of the data transmissions, a reordering depth of 10 TTI (e.g., 10 PDUs sent on MCG in 1 ms, but another 10 PDUs sent on SCG in 10 ms). The UE is mandated to ensure a maximum reordering-depth of 5 ms, however. Therefore, after the first 1 ms, the UE has 4 ms left to transmit the remaining data and should thus move the wrongly pre-processed data for the SCG to the MCG RLC for transmission there, involving a re-processing of the PDUs.

In some embodiments, the data volume is to be compared to the PDCP split threshold, considering that pre-processing is allowed. When PDCP PDUs are moved to RLC for the purpose of pre-processing, and the data is not yet transmitted, the data volume calculation could still be compared to the split threshold. The threshold determines the amount of data buffered for transmission on the prioritized uplink transmission path, and thus all data on both RLC and PDCP that is not yet being transmitted should be considered. In some embodiments, besides PDCP data volume, all pre-processed data that has not yet been transmitted on RLC should be considered for comparison with the PDCP split threshold.

The buffer status reporting (BSR) or data volume reporting more generally may then follow the LTE operation, meaning that if the data volume is below the split threshold, data is indicated only to the configured uplink transmission path. If the data volume is higher than the threshold, data is indicated to both uplink transmission paths. While the data volume for the BSR operation is the same as in LTE, for effective pre-processing implementation, it is noted however that the actual submission to a lower layer procedure would need to be slightly different than in LTE. That is, when the data volume is below the PDCP split threshold, it must be transmitted via the configured uplink transmission path (while in LTE it was possible via either uplink transmission path).

According to certain embodiments, when the data volume is below the PDCP split threshold, the UE is not expected to have data available for transmission on the unprioritized uplink transmission path.

Example text that can be added to TS 38.323 v1.0, to limit the maximum time until a transmission gap is closed, is shown below. The additions are shown in bold.
5.2.1 Transmit Operation
At reception of a PDCP SDU from upper layers, the transmitting PDCP entity shall:
   start the discardTimer associated with this PDCP SDU (if configured);
For a PDCP SDU received from upper layers, the transmitting PDCP entity shall:
   associate the COUNT value corresponding to TX_NEXT to this PDCP SDU;
   NOTE: Associating more than half of the PDCP SN space of contiguous PDCP SDUs with PDCP SNs, when e.g., the PDCP SDUs are discarded or transmitted without acknowledgement, may cause HFN desynchronization problem. How to prevent HFN desynchronization problem is left up to UE implementation.
   perform header compression of the PDCP SDU as specified in the subclause 5.7.4;
   perform integrity protection, and ciphering using the TX_NEXT as specified in the subclause 5.9 and 5.8, respectively;
   set the PDCP SN of the PDCP Data PDU to TX_NEXT modulo $2^{[pdcp\text{-}SN\text{-}Size]}$;
   increment TX_NEXT by one;
   submit the resulting PDCP Data PDU to lower layer as specified below.
When submitting a PDCP Data PDU to lower layer, the transmitting PDCP entity shall:
   if the transmitting PDCP entity is associated with one RLC entity:
     submit the PDCP Data PDU to the associated RLC entity;
   else, if the transmitting PDCP entity is associated with two RLC entities:
     if pdcpDuplication is configured and activated:
       duplicate the PDCP Data PDU and submit the PDCP Data PDU to both associated RLC entities;
     else, if pdcpDuplication is configured but not activated:
       submit the PDCP Data PDU to the configured RLC entity;
     else:
       if the PDCP data volume is less than ul-DataSplitThreshold:
         the PDCP Data PDU shall be made available for transmission to the configured RLC entity;
         when requested by lower layers, submit the PDCP Data PDU to the configured RLC entity;
       else:
         the PDCP Data PDU shall be made available for transmission for each associated RLC entity;
         when requested by lower layers, submit the PDCP Data PDU to one of the requesting associated RLC entity.
   NOTE: For the purpose of pre-processing, when the transmitting PDCP entity is associated with two RLC entities, submission of PDCP PDUs to RLC is allowed under the condition that a potentially introduced transmission gap within subsequent PDCP PDUs among the two associated RLC entities is closed within Xms. When pre-processing is employed, beside PDCP data volume, data volume of not yet transmitted RLC PDUs on the two associated RLC entities is considered to compare with the ul-DataSplitThreshold.

An alternative approach to the UE limiting the pre-processing includes two parts, according to some embodiments. The first part is identifying the RLC entity to which to deliver a PDCP PDU. Note that PDCP PDU and RLC SDU will be used indistinctly throughout this description. A PDCP PDU is what the PDCP entity delivers to the RLC entity. An RLC SDU is what the RLC entity receives from a PDCP entity. The second part is monitoring the PDCP PDU and deciding whether to transmit the PDCP PDU in a second RLC entity.

Identifying the RLC Entity to Deliver a PDCP PDU

The first part, or the identifying of the RLC entity in which to deliver a PDCP PDU, includes two steps. At Step 1, the UE calculates the time to transmit (TtT) an RLC SDU (also called TtT_SDU). This measurement is calculated per each RLC entity. This measurement can be further processed to be used in successive operations and can be, for example, an average, a median, or a maximum TtT for an RLC SDU. TtT an RLC SDU is the time from when the PDCP entity delivers a PDCP PDU to the RLC entity until the RLC entity transmits the full RLC SDU, or when the UE has received a sufficient grant to transmit the full RLC SDU.

At Step 2, the UE decides by which RLC entity a PDCP PDU is delivered first. In general, the UE delivers PDCP PDUs to the RLC entity that has the shortest TtT (instant/mean/median/max). The inequality that is TtT_SDU_1−TtT_SDU_2>offset means that the second RLC entity delivers PDCP PDUs faster than the first RLC entity (the index 1 and 2 hereby relates to the RLC entity or cell group). Thus, the UE may favor transmission of the PDCP PDU by the second RLC entity. The inequality that is offset>TtT_SDU_1−TtT_SDU_2 means that the first RLC entity delivers PDCP PDUs faster than the second RLC entity. Thus, the UE may favor the transmission of a PDCP PDU by the first RLC entity. The inequality that is off-set≤TtT_SDU_1−TtT_SDU_2≤offset means that the transmission of a PDCP PDU by either of the RLC entities happens within the offset window and thus the PDCP entity may deliver the PDCP PDU to either of the RLC entities. With this embodiment, a load balancing among the transmission queues is achieved. TtT_SDU_1 is the (mean/median/max/etc.) TtT an RLC SDU in the first RLC entity, and TtT_SDU_2 is the (mean/median/max/etc.) TtT an RLC SDU in the second RLC entity. The offset is a hardcoded or configured value (by RRC signaling from a gNB).

According to some embodiments, the processing circuitry 120 of UE 110 may be configured to obtain a maximum pre-processing limit for pre-processing PDUs for transmission via the first and/or second uplink transmission paths and perform one or more actions to prevent the pre-processing of PDUs from exceeding the maximum pre-processing limit. This may include discarding a PDU pre-processed for transmission via the first uplink transmission path. This may also include retransmitting, via the second uplink transmission path, the pre-processed PDU that was discarded from transmission via the first uplink transmission path.

The maximum pre-processing limit may include a limit for a transmission time difference between transmission of a first PDU on the first uplink transmission path and transmission of a second PDU on the second uplink transmission path.

The processing circuitry 120 may be configured to perform one or more actions by limiting pre-processing of PDUs by a maximum buffering or queueing time on a first Radio Link Control, RLC, entity, while a previous or subsequent transmission of a PDU takes place on a second RLC entity. The processing circuitry 120 may also be configured to allow pre-processing of PDUs to take place until a transmitter side reordering timer expires, wherein the timer is started when a transmission gap is introduced between transmission of a first PDU and transmission of a subsequent second PDU, and wherein the timer is stopped when the transmission gap is closed.

Pre-processing of PDUs may be allowed before a request from an RLC entity is received. A PDU may be allowed to be submitted to an RLC entity before a request from an RLC entity is received.

Monitoring the PDCP PDU and Deciding Whether to Transmit the PDCP PDU in a Second RLC Entity The second part of the alternative approach involves monitoring the PDCP PDU and deciding whether to transmit or move the PDCP PDU in a second RLC entity. This second part includes Step 3, where the UE monitors and decides if a PDCP PDU that was delivered by a first RLC entity should actually be transmitted by a second RLC entity. In general, the UE can estimate if a PDCP PDU that was delivered to a first RLC entity may be transmitted by a second RLC entity. This can be assessed by considering the following inequalities. TtT_SDU_1+TtT_SDU_2<T_delay−delta, where T_delay is a parameter similar to the T_reordering time parameter. It relates to maximum jitter or maximum introduced reordering time at the transmitter and may be configurable by RRC.

TtT_SDU_1+TtT_SDU_2>T_delay means that if the PDCP PDU that was buffered in a first RLC entity and later transmitted in a second RLC entity, the PDCP PDU might arrive after T_delay expires on the receiver side. That implies that the PDCP PDU would be discarded. Therefore, when TTT_SDU_1+TTT_SDU_2>T_delay the UE might not attempt to transmit a PDCP PDU by a second RLC entity after it buffered the PDCP PDU in a first RLC entity.

TTT_SDU_1+TTT_SDU_2≤T_delay means that if the a PDCP PDU that was buffered in a first RLC entity and later transmitted in a second RLC entity, the PDCP PDU might arrive before T_delay expires in the receiver side. This implies that the PDCP PDU would still be accepted. Therefore, when TTT_SDU_1+TTT_SDU_2≤T_delay, the UE may still attempt to deliver a PDCP PDU by a second RLC entity if the first RLC entity does not transmit the PDCP PDU after a period of time.

While the inequality TTT_SDU_1+TTT_SDU_2≤T_delay is met, the UE starts a timer (Waiting_timer) when a PDCP PDU is transmitted to a first RLC entity. When the inequality Waiting timer=T_delay−TTT_SDU_2, the PDU entity delivers the PDCP PDU to a second RLC entity. In order to avoid ping-pong between RLC entities, the equation may introduce a delta factor, such as Waiting timer=T_delay−TTT_SDU_2−delta_1. The delta could be different in the case where the PDCP PDU is first transmitted over a first RLC entity and it is later decided that the PDU is to be transmitted over a second RLC entity. This equation could be Waiting timer=T_delay−TTT_SDU_1−delta_2.

In order to minimize UE processing, a UE may initiate a measurement/timer for every n PDCP PDUs or for every time there is a transmission gap. For example, if a measurement is initiated every n PDCP PDUs, the decision made in Step 2 and Step 3 may apply for all PDCP PDUs with SN=X and SN=X+n−1. Similarly, if the timer is started when there is a gap, the decision made in Step 2 and Step 3 should apply to all PDUs until the next gap. A combination of the two approaches can be also be used.

In a further embodiment, in addition to the method described in this subsection that leads to more balanced data queues and thus lower reordering delays/jitter, the UE may further limit the absolute amount of pre-processing per queue by not pre-processing for a particular RLC entity, if the amount of data buffered for an RLC entity is higher than a configured threshold, or not pre-processing for an RLC entity, if TtT_SDU for this RLC entity is higher than a configured threshold.

There are two lines of thought. On one hand, PDCP PDUs should not be submitted to RLC entities for transmission unless an uplink grants is received. This thought reuses the LTE threshold-based mechanism for UL split bearer. To uphold operator and network control, it should not be the UE that decides upon the UL transmission path for a PDCP PDU. In this case, the path needs to be determined before the UL grant is received to allow efficient pre-processing in some implementations. Pre-processing, or determining UL transmission direction by the UE, may lead to extensive reordering delays at the PDCP receiver, if the pre-determined UL split ratio does not correspond to the UL grant ratio. That is, the introduced jitter by the reordering delays becomes UE implementation specific. There may be additional standardization complexity in handling or discarding data on the RLC layer, reconfiguration of the prioritized UL path, or dynamic reconfiguration of PDCP UL duplication. The effective switch/duplication activation/deactivation time could be delayed by the pre-processed data on one RLC, which cannot be made available for transmission/duplication on the other RLC.

However, on the other hand, submitting PDCP PDUs to the RLC only upon request may cause a significant burden in order to enable efficient pre-processing. Some embodiments described herein provide solutions that avoid the bad UE behaviour, which may include not pre-processing according to a grant ratio (leading to reordering delays) or having pre-processed data for one UL direction get stuck when no further grant can be issued (leading to eventual data loss).

It is recognized herein that since the UE cannot estimate the gNBs scheduling behaviour entirely, leaving the pre-processing in UL split bearer to the UE is not feasible. Bad UE behaviour can be avoided by limiting the maximum time until a transmission gap is closed by the transmitter (maximum time to transmit PDCP PDU n after transmission of PDCP n+1).

In some embodiments, the PDCP of the UE ensures that not more than half of the PDCP SN space is allocated. Duplication may also be applicable to a PDCP Control PDU.

According to some embodiments, the processing circuitry 120 is configured to operate in an uplink split-bearer configuration to transmit PDU by a first RLC entity via a first uplink transmission path or by a second RLC entity via a second uplink transmission path. The processing circuitry 120 is configured to identify which one of the first and second RLC entities will deliver a first PDU, buffer the first PDU in the identified RLC identity of the first and second RLC entities, monitor pre-processing of the first PDU in the identified RLC identity and determine, based on the monitoring, whether to transmit the first PDU in the other one of the first and second RLC entities.

The identification of which one of the first and second RLC entities will deliver the first PDU may include calculating a time to transit a full RLC Service Data Unit, SDU, for the first and second RLC entities, wherein the time to transit for the RLC SDU comprises the time from when a RDU is delivered to the respective RLC entity until when the respective RLC entity transmits the full RLC SDU or when the UE has received a sufficient grant to transmit the full RLC SDU. The processing circuitry 120 may also be configured to determine which of the first and second RLC entities to deliver the first PDU, based on the time to transit for each of the first and second RLC entities. It may be determined that the first PDU is to be transmitted in the other one of the first and second RLC entities in response to determining that a sum of the time to transit for the first RLC entity and the time to transit for the second RLC entity is less than a predetermined time delay threshold.

Figure 6:
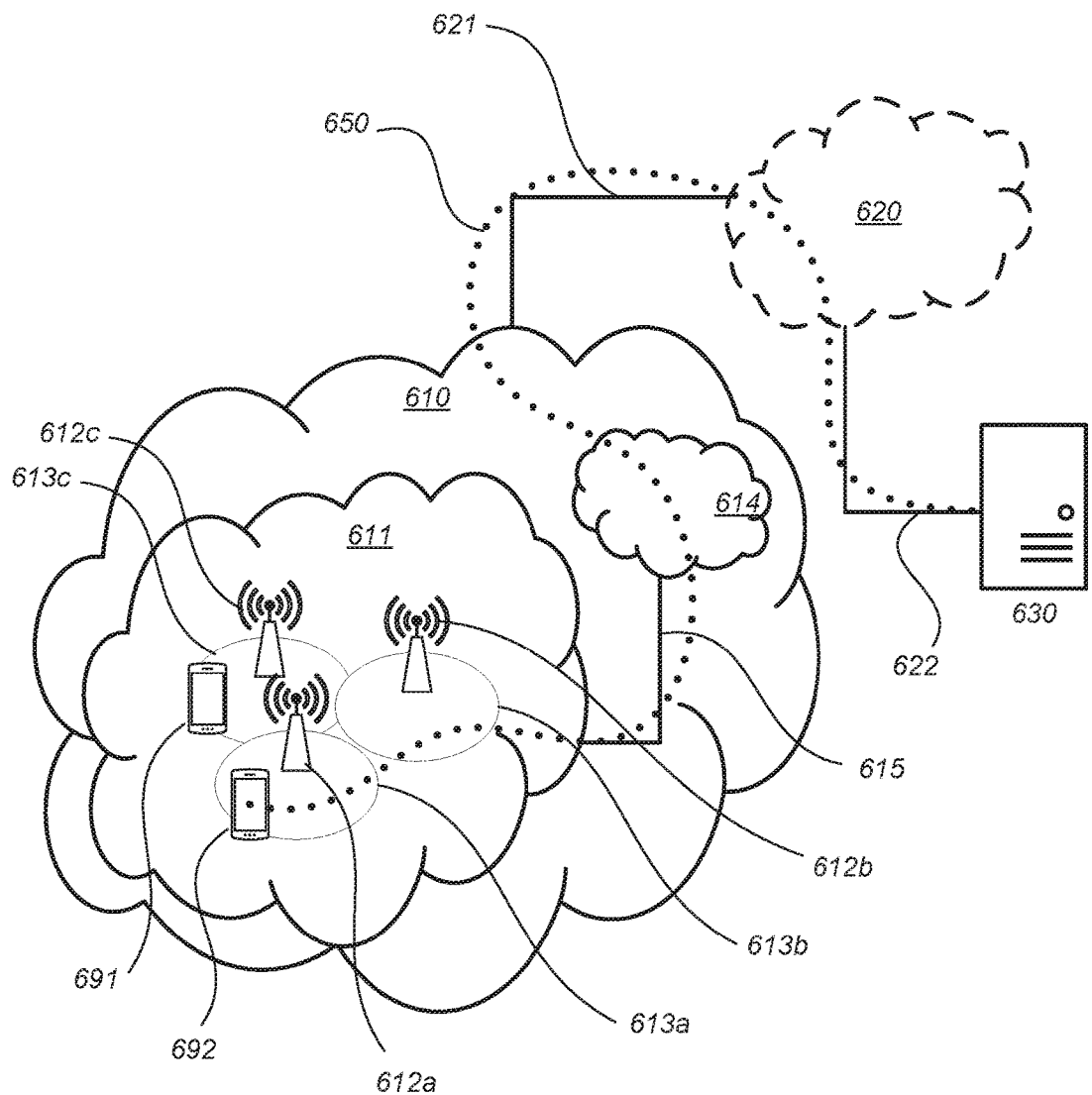
FIG. 6 schematically illustrates a telecommunication network connected via an intermediate network to a host computer, according to some embodiments.

FIG. 6 illustrates a telecommunications network connected via an intermediate network to a host computer in accordance with some embodiments. With reference to FIG. 6, in accordance with an embodiment, a communication system includes telecommunication network 610, such as a 3GPP-type cellular network, which comprises access network 611, such as a radio access network, and core network 614. Access network 611 comprises a plurality of base stations 612a, 612b, 612c, such as NBs, eNBs, gNBs or other types of wireless access points, each defining a corresponding coverage area 613a, 613b, 613c. Each base station 612a, 612b, 612c is connectable to core network 614 over a wired or wireless connection 615. A first UE 691 located in coverage area 613c is configured to wirelessly connect to, or be paged by, the corresponding base station 612c. A second UE 692 in coverage area 613a is wirelessly connectable to the corresponding base station 612a. While a plurality of UEs 691, 692 are illustrated in this example, the disclosed embodiments are equally applicable to a situation where a sole UE is in the coverage area or where a sole UE is connecting to the corresponding base station 612.

Telecommunication network 610 is itself connected to host computer 630, which may be embodied in the hardware and/or software of a standalone server, a cloud-implemented server, a distributed server or as processing resources in a server farm. Host computer 630 may be under the ownership or control of a service provider, or may be operated by the service provider or on behalf of the service provider. Connections 621 and 622 between telecommunication network 610 and host computer 630 may extend directly from core network 614 to host computer 630 or may go via an optional intermediate network 620. Intermediate network 620 may be one of, or a combination of more than one of, a public, private or hosted network; intermediate network 620, if any, may be a backbone network or the Internet; in particular, intermediate network 620 may comprise two or more sub-networks (not shown).

The communication system of FIG. 6 as a whole enables connectivity between the connected UEs 691, 692 and host computer 630. The connectivity may be described as an over-the-top (OTT) connection 660. Host computer 630 and the connected UEs 691, 692 are configured to communicate data and/or signaling via OTT connection 650, using access network 611, core network 614, any intermediate network 620 and possible further infrastructure (not shown) as intermediaries. OTT connection 650 may be transparent in the sense that the participating communication devices through which OTT connection 650 passes are unaware of routing of uplink and downlink communications. For example, base station 612 may not or need not be informed about the past routing of an incoming downlink communication with data originating from host computer 630 to be forwarded (e.g., handed over) to a connected UE 691. Similarly, base station 612 need not be aware of the future routing of an outgoing uplink communication originating from the UE 691 towards the host computer 630.

Example implementations, in accordance with an embodiment, of the UE, base station and host computer discussed in the preceding paragraphs will now be described with reference to FIG. 7, which illustrates a host computer communicating via a base station with a user equipment over a partially wireless connection in accordance with some embodiments. In communication system 700, host computer 710 comprises hardware 715 including communication interface 716 configured to set up and maintain a wired or wireless connection with an interface of a different communication device of communication system 700. Host computer 710 further comprises processing circuitry 718, which may have storage and/or processing capabilities. In particular, processing circuitry 718 may comprise one or more programmable processors, application-specific integrated circuits, field programmable gate arrays or combinations of these (not shown) adapted to execute instructions. Host computer 710 further comprises software 711, which is stored in or accessible by host computer 710 and executable by processing circuitry 718. Software 711 includes host application 712. Host application 712 may be operable to provide a service to a remote user, such as UE 730 connecting via OTT connection 750 terminating at UE 730 and host computer 710. In providing the service to the remote user, host application 712 may provide user data which is transmitted using OTT connection 750.

Communication system 700 further includes base station 720 provided in a telecommunication system and comprising hardware 725 enabling it to communicate with host computer 710 and with UE 730. Hardware 725 may include communication interface 726 for setting up and maintaining a wired or wireless connection with an interface of a different communication device of communication system 700, as well as radio interface 727 for setting up and maintaining at least wireless connection 770 with UE 730 located in a coverage area (not shown in FIG. 7) served by base station 720. Communication interface 726 may be configured to facilitate connection 770 to host computer 710. Connection 770 may be direct or it may pass through a core network (not shown in FIG. 7) of the telecommunication system and/or through one or more intermediate networks outside the telecommunication system. In the embodiment shown, hardware 725 of base station 720 further includes processing circuitry 728, which may comprise one or more programmable processors, application-specific integrated circuits, field programmable gate arrays or combinations of these (not shown) adapted to execute instructions. Base station 720 further has software 721 stored internally or accessible via an external connection.

Communication system 700 further includes UE 730 already referred to. Its hardware 735 may include radio interface 737 configured to set up and maintain wireless connection 760 with a base station serving a coverage area in which UE 730 is currently located. Hardware 735 of UE 730 further includes processing circuitry 738, which may comprise one or more programmable processors, application-specific integrated circuits, field programmable gate arrays or combinations of these (not shown) adapted to execute instructions. UE 730 further comprises software 731, which is stored in or accessible by UE 730 and executable by processing circuitry 738. Software 731 includes client application 732. Client application 732 may be operable to provide a service to a human or non-human user via UE 730, with the support of host computer 710. In host computer 710, an executing host application 712 may communicate with the executing client application 732 via OTT connection 750 terminating at UE 730 and host computer 710. In providing the service to the user, client application 732 may receive request data from host application 712 and provide user data in response to the request data. OTT connection 750 may transfer both the request data and the user data. Client application 732 may interact with the user to generate the user data that it provides.

Figure 7:
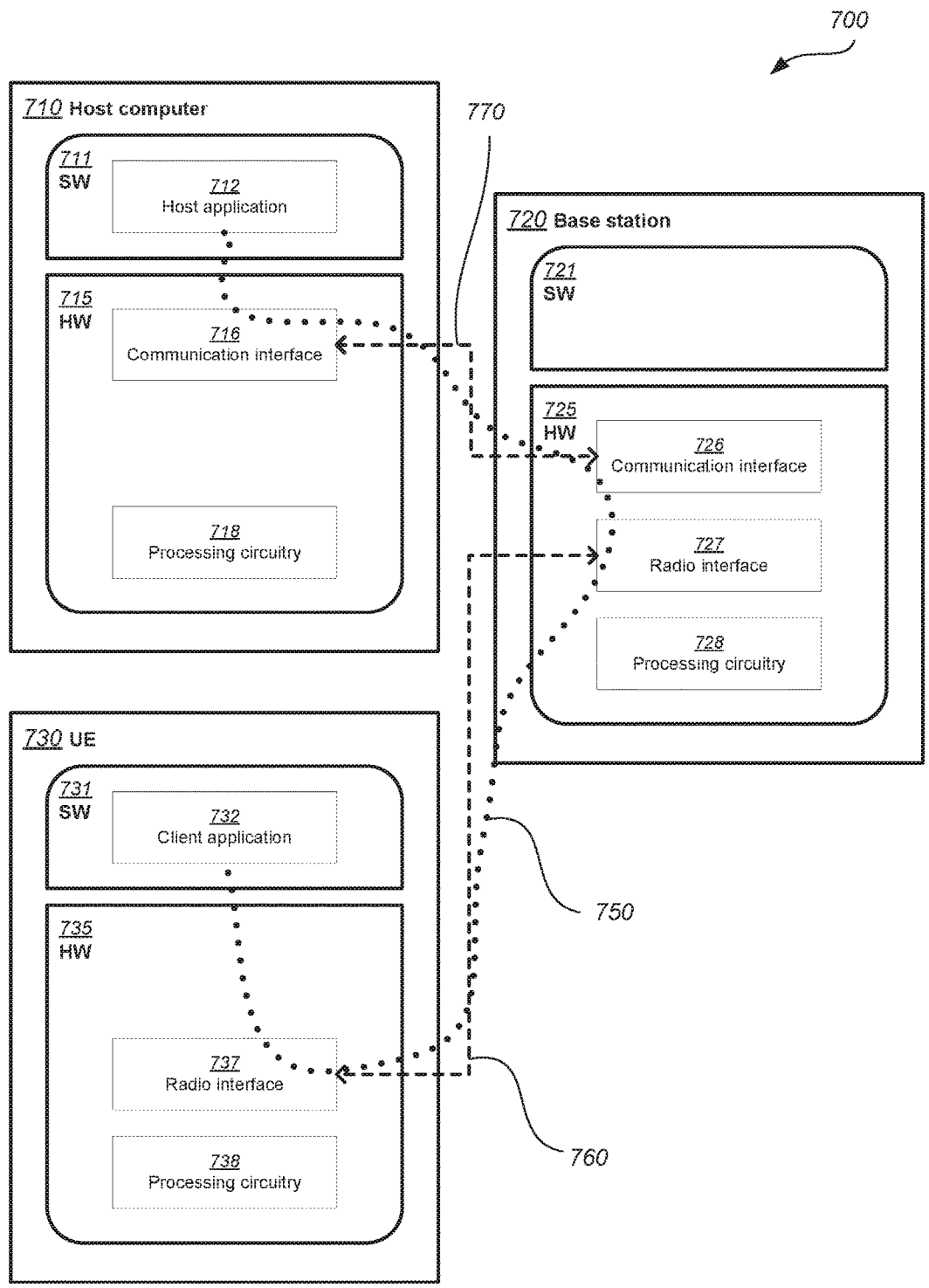
FIG. 7 is a generalized block diagram of a host computer communicating via a base station with a user equipment over a partially wireless connection, according to some embodiments.

It is noted that host computer 710, base station 720 and UE 730 illustrated in FIG. 7 may be similar or identical to host computer 630, one of base stations 612a, 612b, 612c and one of UEs 691, 692 of FIG. 6, respectively. This is to say, the inner workings of these entities may be as shown in FIG. 7 and independently, the surrounding network topology may be that of FIG. 6.

In FIG. 7, OTT connection 750 has been drawn abstractly to illustrate the communication between host computer 710 and UE 730 via base station 720, without explicit reference to any intermediary devices and the precise routing of messages via these devices. Network infrastructure may determine the routing, which it may be configured to hide from UE 730 or from the service provider operating host computer 710, or both. While OTT connection 750 is active, the network infrastructure may further take decisions by which it dynamically changes the routing (e.g., on the basis of load balancing consideration or reconfiguration of the network).

Wireless connection 760 between UE 730 and base station 720 is in accordance with the teachings of the embodiments described throughout this disclosure. One or more of the various embodiments improve the performance of OTT services provided to UE 730 using OTT connection 750, in which wireless connection 760 forms the last segment. UE bad behavior may be reduced and the time between receiving an uplink grant and the time a un uplink transmission is sent may also be reduced. More precisely, the teachings of these embodiments may improve the data rate, latency, and power consumption and thereby provide benefits such as reduced user waiting time, better responsiveness, and extended battery lifetime.

A measurement procedure may be provided for the purpose of monitoring data rate, latency and other factors on which the one or more embodiments improve. There may further be an optional network functionality for reconfiguring OTT connection 750 between host computer 710 and UE 730, in response to variations in the measurement results. The measurement procedure and/or the network functionality for reconfiguring OTT connection 750 may be implemented in software 711 and hardware 715 of host computer 710 or in software 731 and hardware 735 of UE 730, or both. In embodiments, sensors (not shown) may be deployed in or in association with communication devices through which OTT connection 750 passes; the sensors may participate in the measurement procedure by supplying values of the monitored quantities exemplified above, or supplying values of other physical quantities from which software 711, 731 may compute or estimate the monitored quantities. The reconfiguring of OTT connection 750 may include message format, retransmission settings, preferred routing etc.; the reconfiguring need not affect base station 720, and it may be unknown or imperceptible to base station 720. Such procedures and functionalities may be known and practiced in the art. In certain embodiments, measurements may involve proprietary UE signaling facilitating host computer 710's measurements of throughput, propagation times, latency and the like. The measurements may be implemented in that software 711 and 731 causes messages to be transmitted, in particular empty or 'dummy' messages, using OTT connection 750 while it monitors propagation times, errors etc.

Figure 8:
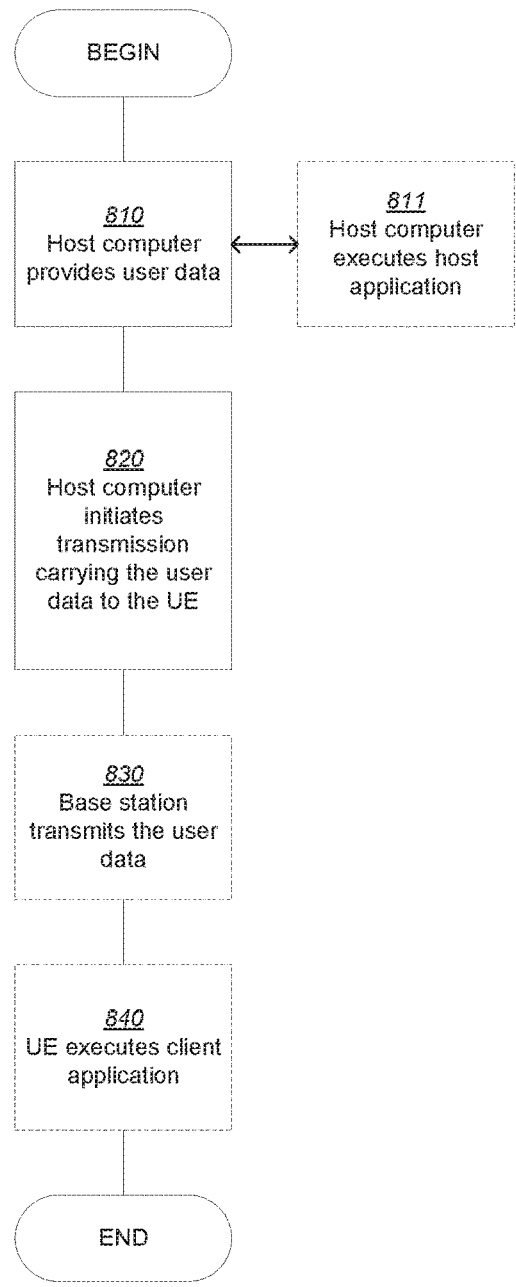
FIGS. 8 to 11 are flowcharts illustrating example methods implemented in a communication system including a host computer, a base station and a user equipment.

FIG. 8 is a flowchart illustrating a method implemented in a communication system, in accordance with one embodiment. The communication system includes a host computer, a base station and a UE which may be those described with reference to FIGS. 6 and 7. For simplicity of the present disclosure, only drawing references to FIG. 8 will be included in this section. In step 810, the host computer provides user data. In substep 811 (which may be optional) of step 810, the host computer provides the user data by executing a host application. In step 820, the host computer initiates a transmission carrying the user data to the UE. In step 830 (which may be optional), the base station transmits to the UE the user data which was carried in the transmission that the host computer initiated, in accordance with the teachings of the embodiments described throughout this disclosure. In step 840 (which may also be optional), the UE executes a client application associated with the host application executed by the host computer.

Figure 9:
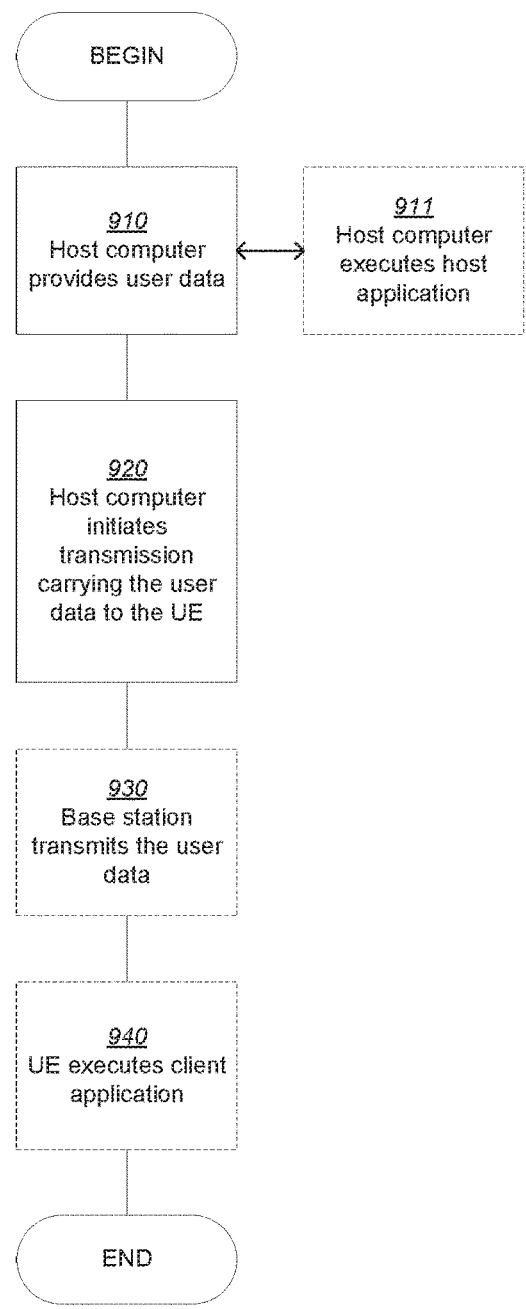

FIG. 9 is a flowchart illustrating a method implemented in a communication system, in accordance with one embodiment. The communication system includes a host computer, a base station and a UE which may be those described with reference to FIGS. 6 and 7. For simplicity of the present disclosure, only drawing references to FIG. 9 will be included in this section. In step 910 of the method, the host computer provides user data. In an optional substep (not shown) the host computer provides the user data by executing a host application. In step 920, the host computer initiates a transmission carrying the user data to the UE. The transmission may pass via the base station, in accordance with the teachings of the embodiments described throughout this disclosure. In step 930 (which may be optional), the UE receives the user data carried in the transmission.

Figure 10:
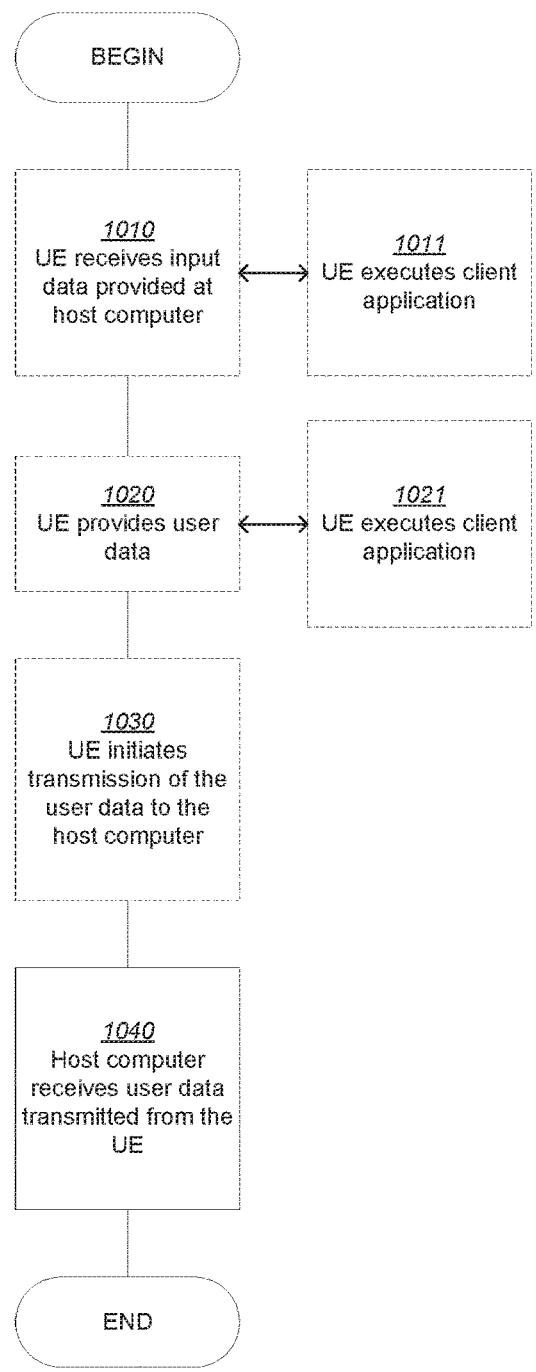

FIG. 10 is a flowchart illustrating a method implemented in a communication system, in accordance with one embodiment. The communication system includes a host computer, a base station and a UE which may be those described with reference to FIGS. 6 and 7. For simplicity of the present disclosure, only drawing references to FIG. 10 will be included in this section. In step 1010 (which may be optional), the UE receives input data provided by the host computer. Additionally or alternatively, in step 1020, the UE provides user data. In substep 1021 (which may be optional) of step 1020, the UE provides the user data by executing a client application. In substep 1011 (which may be optional) of step 1010, the UE executes a client application which provides the user data in reaction to the received input data provided by the host computer. In providing the user data, the executed client application may further consider user input received from the user. Regardless of the specific manner in which the user data was provided, the UE initiates, in substep 1030 (which may be optional), transmission of the user data to the host computer. In step 1040 of the method, the host computer receives the user data transmitted from the UE, in accordance with the teachings of the embodiments described throughout this disclosure.

Figure 11:
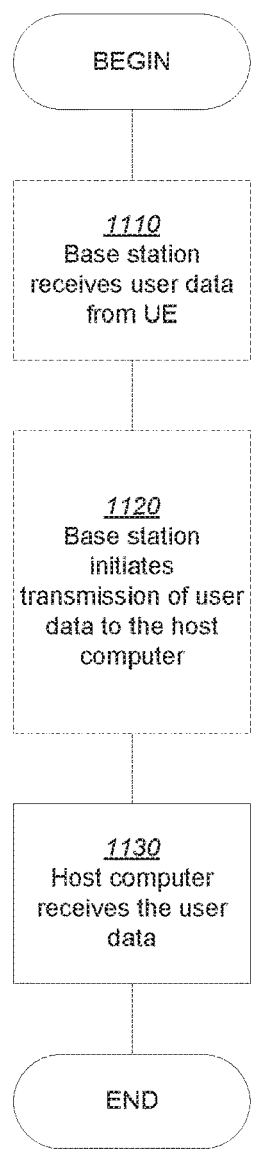

FIG. 11 is a flowchart illustrating a method implemented in a communication system, in accordance with one embodiment. The communication system includes a host computer, a base station and a UE which may be those described with reference to FIGS. 6 and 7. For simplicity of the present disclosure, only drawing references to FIG. 11 will be included in this section. In step 1110 (which may be optional), in accordance with the teachings of the embodiments described throughout this disclosure, the base station receives user data from the UE. In step 1120 (which may be optional), the base station initiates transmission of the received user data to the host computer. In step 1130 (which may be optional), the host computer receives the user data carried in the transmission initiated by the base station.

Any appropriate steps, methods, features, functions, or benefits disclosed herein may be performed through one or more functional units or modules of one or more virtual apparatuses. Each virtual apparatus may comprise a number of these functional units. These functional units may be implemented via processing circuitry, which may include one or more microprocessor or microcontrollers, as well as other digital hardware, which may include digital signal processors (DSPs), special-purpose digital logic, and the like. The processing circuitry may be configured to execute program code stored in memory, which may include one or several types of memory such as read-only memory (ROM), random-access memory (RAM), cache memory, flash memory devices, optical storage devices, etc. Program code stored in memory includes program instructions for executing one or more telecommunications and/or data communications protocols as well as instructions for carrying out one or more of the techniques described herein. In some implementations, the processing circuitry may be used to cause the respective functional unit to perform corresponding functions according one or more embodiments of the present disclosure.

Figure 12:
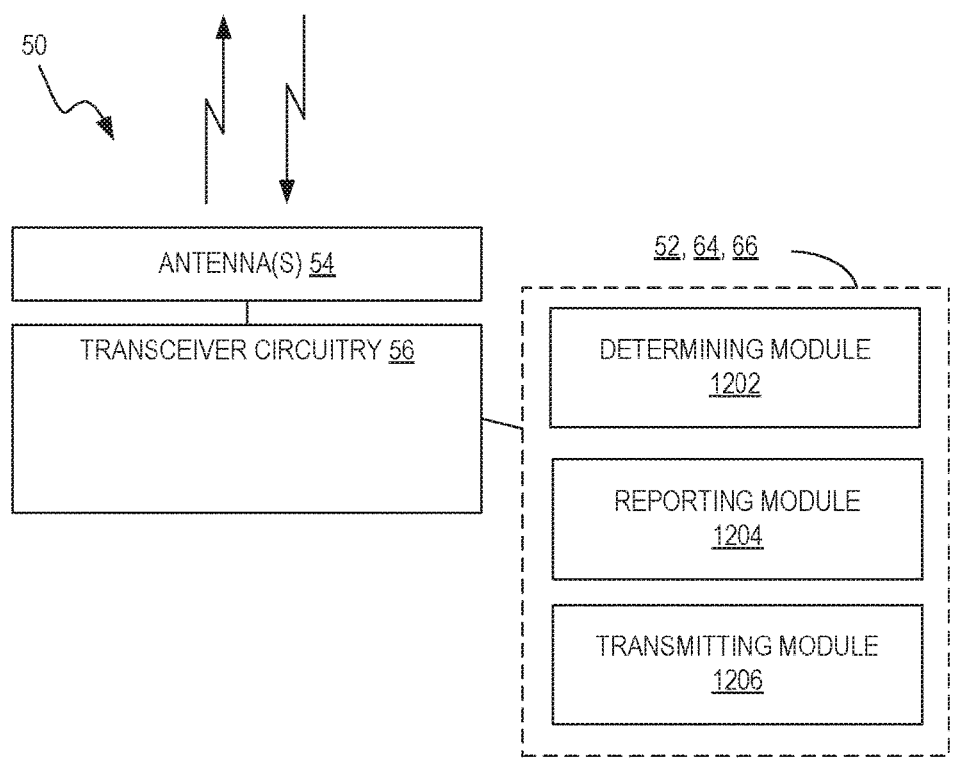
FIG. 12 is a block diagram illustrating a functional implementation of a UE, according to some embodiments.

Accordingly, FIG. 12 shows a functional implementation of a UE, according to some embodiments, configured in an uplink split-bearer configuration to transmit PDUs by a first RLC entity via a first uplink transmission path and/or by a second RLC entity via a second uplink transmission path. The implementation includes a determining module 1202 for determining a total amount of data volume buffered for PDU transmission, where the total amount of data volume includes PDCP data volume and RLC data volume pending for initial transmission in the two RLC entities. The implementation also includes a reporting module 1204 for reporting the PDCP data volume to at least the first uplink transmission path, based on whether the total amount of data volume meets or exceeds a first threshold. The reporting includes, in response to determining that the total amount of data volume meets or exceeds the first threshold, indicating the PDCP data volume to both the first uplink transmission path and the second uplink transmission path, and, in response to determining that the total amount of data volume does not meet the first threshold, indicating the PDCP data volume to only the first uplink transmission path. In some embodiments, the implementation includes a transmitting module 1206 for, in response to determining that the total amount of data volume does not meet a first threshold, submitting the PDCP data volume only to the first RLC entity.

Figure 13:
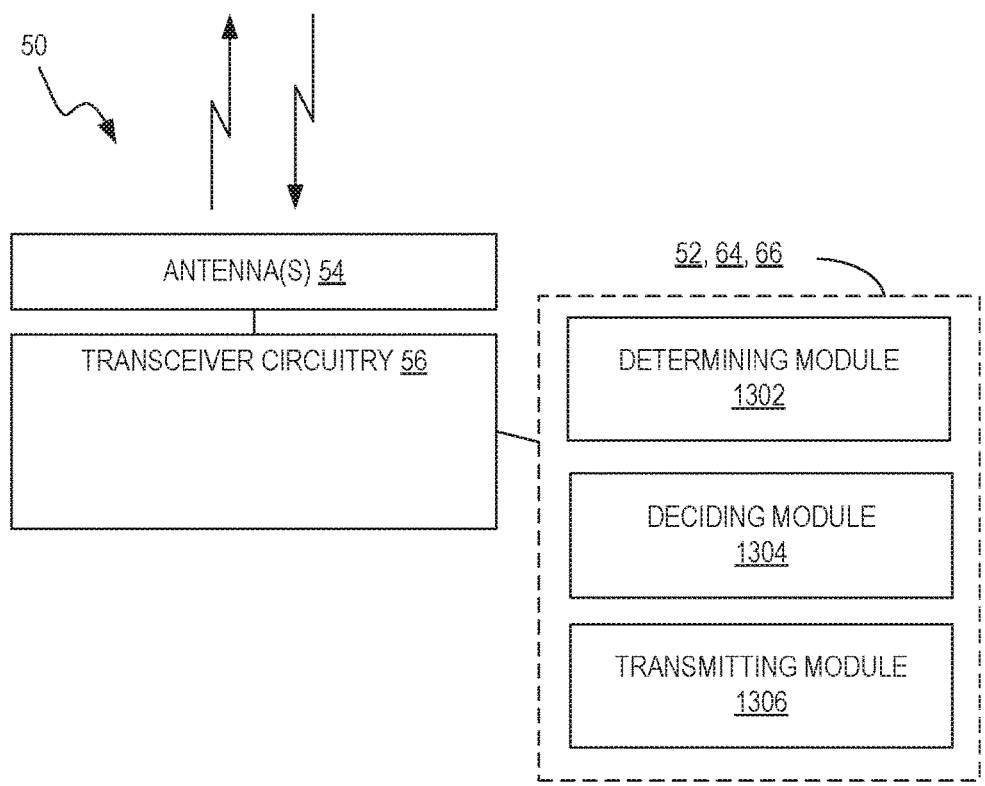
FIG. 13 is a block diagram illustrating another functional implementation of a UE, according to some embodiments.

FIG. 13 shows another functional implementation of a UE, according to some embodiments, configured to transmit PDUs by a first RLC entity via a first uplink transmission path and/or by a second RLC entity via a second uplink transmission path. The implementation includes a determining module 1302 for determining a total amount of data volume buffered for PDU transmission, where the total amount of data volume includes PDCP data volume and RLC data volume pending for initial transmission in the two RLC entities. The implementation also includes a deciding module 1304 for deciding whether submission of the PDCP data volume is allowed to either of the two RLC entities or to only the first RLC entity, based on whether the total amount of data volume meets or exceeds a first threshold. The deciding includes, in response to determining that the total amount of data volume meets or exceeds the first threshold, deciding that the PDCP data volume is allowed to be submitted to either of the two RLC entities, and, in response to determining that the total amount of data volume does not meet the first threshold, deciding that the PDCP data volume is allowed to be submitted to only the first RLC entity. In some embodiments, the implementation includes a transmitting module 1306 for submitting the PDCP data volume according to the deciding.

It will be appreciated that the various methods and embodiments described above are used for illustrative purposes, and variations may occur. For instance, various steps may be combined, omitted, or reordered as necessary to achieve the desired goals. Generally, all terms used herein are to be interpreted according to their ordinary meaning in the relevant technical field, unless a different meaning is clearly given and/or is implied from the context in which it is used. All references to a/an/the element, apparatus, component, means, step, etc. are to be interpreted openly as referring to at least one instance of the element, apparatus, component, means, step, etc., unless explicitly stated otherwise. The steps of any methods disclosed herein do not have to be performed in the exact order disclosed, unless a step is explicitly described as following or preceding another step and/or where it is implicit that a step must follow or precede another step. Any feature of any of the embodiments disclosed herein may be applied to any other embodiment, wherever appropriate. Likewise, any advantage of any of the embodiments may apply to any other embodiments, and vice versa. Other objectives, features and advantages of the enclosed embodiments will be apparent from the description.

What is claimed is:

1. A method by a user equipment (UE) configured to transmit packet data units (PDUs) by a first Radio Link Control (RLC) entity via a first uplink transmission path and by a second RLC entity via a second uplink transmission path, the method comprising:
    determining a total amount of data volume buffered for PDU transmission, wherein the total amount of data volume comprises RLC PDU data volume pending for initial transmission in the two RLC entities and Packet Data Convergence Protocol (PDCP) service data unit (SDU) and PDU data volume;
    deciding whether submission of the PDCP SDU and PDU data volume is allowed to both of the first uplink transmission path and the second uplink transmission path or to only the first uplink transmission path, based on whether the total amount of data volume meets or exceeds a first threshold; and
    reporting the PDCP SDU and PDU data volume to at least the first uplink transmission path, wherein the reporting comprises:
        in response to determining that the total amount of data volume meets or exceeds the first threshold, indicating the PDCP SDU and PDU data volume to both the first uplink transmission path and the second uplink transmission path, and
        in response to determining that the total amount of data volume does not meet the first threshold, indicating the PDCP SDU and PDU data volume to only the first uplink transmission path.

2. The method according to claim 1, wherein the first uplink transmission path is a prioritized uplink transmission path and the second uplink transmission path is an unprioritized uplink transmission path.

3. The method according to claim 1, wherein the first RLC entity belongs to a Master Cell Group (MCG) and the second RLC entity belongs to a Secondary Cell Group (SCG).

4. The method according to claim 1, further comprising, in response to determining that the total amount of data volume does not meet the first threshold, submitting the PDCP SDU and PDU data volume only to the first RLC entity.

5. The method according to claim 1, wherein the first uplink transmission path corresponds to a MAC entity associated with the first RLC entity, and wherein the second uplink transmission path corresponds to a MAC entity associated with the second RLC entity.

6. A user equipment (UE) configured to transmit packet data units (PDUs) by a first Radio Link Control (RLC) entity via a first uplink transmission path and by a second RLC entity via a second uplink transmission path, the UE comprising:
    transceiver circuitry configured to send and receive radio signals; and
    processing circuitry operatively associated with the transceiver circuitry and configured to:
        determine a total amount of data volume buffered for PDU transmission, wherein the total amount of data volume comprises RLC PDU data volume pending for initial transmission in the two RLC entities and Packet Data Convergence Protocol (PDCP) service data unit (SDU) and PDU data volume;
        decide whether submission of the PDCP SDU and PDU data volume is allowed to both of the first uplink transmission path and the second uplink transmission path or to only the first uplink transmission path, based on whether the total amount of data volume meets or exceeds a first threshold; and
        report the PDCP SDU and PDU data volume to at least the first uplink transmission path, wherein the reporting comprises:
            in response to determining that the total amount of data volume meets or exceeds the first threshold, indicating the PDCP SDU and PDU data volume to both the first uplink transmission path and the second uplink transmission path, and
            in response to determining that the total amount of data volume does not meet the first threshold, indicating the PDCP SDU and PDU data volume to only the first uplink transmission path.

7. The UE according to claim 6, wherein the first uplink transmission path is a prioritized uplink transmission path and the second uplink transmission path is an unprioritized uplink transmission path.

8. The UE according to claim 6, wherein the first RLC entity belongs to a Master Cell Group (MCG) and the second RLC entity belongs to a Secondary Cell Group (SCG).

9. The UE according to claim 6, wherein the processing circuitry is configured to, in response to determining that the total amount of data does not meet the first threshold, submit the PDCP SDU and PDU data volume only to the first RLC entity.

10. The UE according to claim 6, wherein the first uplink transmission path corresponds to a MAC entity associated with the first RLC entity, and wherein the second uplink transmission path corresponds to a MAC entity associated with the second RLC entity.

11. A method by a user equipment (UE) configured to transmit packet data units (PDUs) by a first Radio Link Control (RLC) entity via a first uplink transmission path and by a second RLC entity via a second uplink transmission path, the method comprising:
    determining a total amount of data volume buffered for PDU transmission, wherein the total amount of data volume comprises RLC PDU data volume pending for initial transmission in the two associated RLC entities and Packet Data Convergence Protocol (PDCP) service data unit (SDU) and PDU data volume; and
    deciding whether submission of the PDCP SDU and PDU data volume is allowed to either of the two RLC entities or to only the first RLC entity, based on whether the total amount of data volume meets or exceeds a first threshold, wherein the deciding comprises:
        in response to determining that the total amount of data volume meets or exceeds the first threshold, deciding that the PDCP SDU and PDU data volume is allowed to be submitted to either of the two RLC entities, and
        in response to determining that the total amount of data volume does not meet the first threshold, deciding that the PDCP SDU and PDU data volume is allowed to be submitted to only the first RLC entity.

12. The method according to claim 11, further comprising submitting the PDCP SDU and PDU data volume according to the decision.

13. The method according to claim 11, further comprising, in response to deciding that the PDCP SDU and PDU data volume is allowed to be submitted to either of the two RLC entities, submitting the PDCP SDU and PDU data volume to whichever of the two RLC entities requested the PDCP SDU and PDU data volume.

14. The method according to claim 11, wherein the first uplink transmission path is a prioritized uplink transmission path and the second uplink transmission path is an unprioritized uplink transmission path.

15. The method according to claim 11, wherein the first RLC entity belongs to a Master Cell Group (MCG) and the second RLC entity belongs to a Secondary Cell Group (SCG).

16. The method according to claim 11, wherein the first uplink transmission path corresponds to a MAC entity associated with the first RLC entity, and wherein the second uplink transmission path corresponds to a MAC entity associated with the second RLC entity.

17. A user equipment (UE) configured to transmit packet data units (PDUs) by a first Radio Link Control (RLC) entity via a first uplink transmission path and by a second RLC entity via a second uplink transmission path, the UE comprising:
    transceiver circuitry configured to send and receive radio signals; and
    processing circuitry operatively associated with the transceiver circuitry and configured to:
        determine a total amount of data volume buffered for PDU transmission, wherein the total amount of data volume comprises RLC PDU data volume pending for initial transmission in the two RLC entities and Packet Data Convergence Protocol (PDCP) service data unit (SDU) and PDU data volume; and
        decide whether submission of the PDCP SDU and PDU data volume is allowed to either of the two RLC entities or to only the first RLC entity, based on whether the total amount of data volume meets or exceeds a first threshold, wherein the processing circuitry is configured to:
            in response to determining that the total amount of data volume meets or exceeds the first threshold, decide that the PDCP SDU and PDU data volume is allowed to be submitted to either of the two RLC entities, and
            in response to determining that the total amount of data volume does not meet the first threshold, decide that the PDCP SDU and PDU data volume is allowed to be submitted to only the first RLC entity.

18. The UE according to claim 17, wherein the processing circuitry is configured to submit the PDCP SDU and PDU data volume according to the decision.

19. The UE according to claim 17, wherein the processing circuitry is configured to, in response to deciding that the PDCP SDU and PDU data volume is allowed to be submitted to either of the two RLC entities, submit the PDCP SDU and PDU data volume to whichever of the two RLC entities requested the PDCP SDU and PDU data volume.

20. The UE according to claim 17, wherein the first uplink transmission path is a prioritized uplink transmission path and the second uplink transmission path is an unprioritized uplink transmission path.

21. The UE according to claim 17, wherein the first RLC entity belongs to a Master Cell Group (MCG) and the second RLC entity belongs to a Secondary Cell Group (SCG).

22. The UE according to claim 17, wherein the first uplink transmission path corresponds to a MAC entity associated with the first RLC entity, and wherein the second uplink transmission path corresponds to a MAC entity associated with the second RLC entity.

* * * * *

UNITED STATES PATENT AND TRADEMARK OFFICE
CERTIFICATE OF CORRECTION

| | |
|---|---|
| PATENT NO. | : 10,492,241 B2 |
| APPLICATION NO. | : 16/227430 |
| DATED | : November 26, 2019 |
| INVENTOR(S) | : Pradas et al. |

Page 1 of 1

It is certified that error appears in the above-identified patent and that said Letters Patent is hereby corrected as shown below:

In the Specification

In Column 24, Line 28, delete "one of the" and insert -- the --, therefor.

Signed and Sealed this
Nineteenth Day of May, 2020

Andrei Iancu
*Director of the United States Patent and Trademark Office*